(12) United States Patent
Kim et al.

(10) Patent No.: US 11,879,896 B2
(45) Date of Patent: *Jan. 23, 2024

(54) THERAPEUTIC PROTEIN SELECTION IN SIMULATED IN VIVO CONDITIONS

(71) Applicant: Regeneron Pharmaceuticals, Inc., Tarrytown, NY (US)

(72) Inventors: Dorothy Kim, Brooklyn, NY (US); Michael Marlow, Greenwich, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/892,618

(22) Filed: Aug. 22, 2022

(65) Prior Publication Data

US 2023/0066527 A1    Mar. 2, 2023

Related U.S. Application Data

(63) Continuation of application No. 16/537,811, filed on Aug. 12, 2019.

(60) Provisional application No. 62/865,446, filed on Jun. 24, 2019, provisional application No. 62/718,307, filed on Aug. 13, 2018.

(51) Int. Cl.
*G01N 33/68* (2006.01)
*G01N 33/53* (2006.01)

(52) U.S. Cl.
CPC ..... *G01N 33/6845* (2013.01); *G01N 33/5306* (2013.01); *G01N 33/6854* (2013.01)

(58) Field of Classification Search
CPC ......... G01N 33/5306; G01N 33/54306; G01N 33/54393; G01N 33/6845; G01N 33/6854
See application file for complete search history.

(56) References Cited

U.S. PATENT DOCUMENTS

| 2014/0105824 A1 | 4/2014 | Shepard et al. |
| 2020/0064353 A1* | 2/2020 | Kim ................. G01N 33/54306 |

FOREIGN PATENT DOCUMENTS

| JP | 1987-071861 A2 | 4/1987 |
| JP | 2009-534466 A2 | 9/2009 |
| JP | 2010-127827 A2 | 6/2010 |
| JP | 2015-508643 A2 | 3/2015 |
| JP | 2015-510761 A2 | 4/2015 |
| JP | 2015-528797 A2 | 10/2015 |
| WO | WO2015/017285 A2 | 2/2015 |
| WO | WO2016/138160 A1 | 9/2016 |
| WO | WO2016164835 A1 | 10/2016 |
| WO | WO2017044933 A1 | 3/2017 |
| WO | WO2018005551 A1 | 1/2018 |

OTHER PUBLICATIONS

Petersen et al., "Strategies Using Bio-Layer Interferometry Biosensor Technology for Vaccine Research and Development," Biosensors, 2017, 7, 49, pp. 1-15.*
Goodell et al., "CaMKII Binding to GluN2B Is Differentially Affected by Macromolecular Crowding Reagents," PLoS ONE, 2014, vol. 9, issue 5, e96522, pp. 1-13.*
Ellis, "Macromolecular crowding: obvious but underappreciated," Trends Biochem. Sci., 2001, vol. 26, No. 10, pp. 597-604.*
Roberts et al., "Specific Ion and Buffer Effects on Protein-Protein Interactions of a Monoclonal Antibody," Mol. Pharmaceutics, 2015, vol. 12, No. 1, pp. 179-193.*
Danlin Yang et al., "Determination of High-Affinity Antibody-antigen Binding Kinetics Using Four Biosensor Platforms," Journal of Visualized Experiments, No. 122, Apr. 17, 2017, pp. 1-16.
David L. Brandon et al., "Milk Matrix Effects on Antibody Binding Analyzed by Enzyme-Linked Immunosorbent Assay and Biolayer Interferometry," Journal of Agricultural and Food Chemistry, vol. 63, No. 13, Mar. 30, 2015, pp. 3593-3598.
Shih Judy et al., "Strategic Approaches for Assessment and Minimization of Matrix Effect in Ligand-Binding Assays," Bioanalysis, Future Science, UK, vol. 6, No. 8, Mar. 31, 2014, pp. 1103-1112.
Christine Bee et al., "Determining the Binding Affinity of Therapeutic Monoclonal Antibodies Towards Their Native Unpurified Antigens in Human Serum," PLOS ONE, vol. 8, No. 11, Nov. 6, 2013, pp. e80501, pp. 1-13.
D. Verzijl et al., "A Novel Label-free Cell-Based Assay Technology Using Biolayer Interferometry," Biosensors and Bioelectronics, vol. 87, Aug. 28, 2016, pp. 388-395.
Dorothy M. Kim et al., "Measuring the Effects of Macromolecular Crowding on Antibody Function with Biolayer Interferometry," MABS, vol. 11, No. 7, Aug. 12, 2019, pp. 1319-1330.
International Search Report, PCT Application No. PCT/US2019/046104, Application Filing Date Aug. 12, 2019, dated Oct. 24, 2019.

(Continued)

*Primary Examiner* — Galina M. Yakovleva
(74) *Attorney, Agent, or Firm* — Kramer Levin Naftalis & Frankel LLP

(57) ABSTRACT

A method of determining the effect of non-specific interactions in simulated in vivo conditions is presently disclosed. The method includes (a) contacting a solution comprising a biologically relevant molecular crowding agent and a target molecule with a biosensor, wherein the surface of the biosensor comprises a capture molecule that specifically binds the target molecule; (b) allowing the target molecule to bind to the capture molecule; and (c) determining an amount of the target molecule bound to capture molecule using biolayer interferometry.

10 Claims, 20 Drawing Sheets

Specification includes a Sequence Listing.

(56) References Cited

OTHER PUBLICATIONS

Search Report for corresponding Singapore Application No. 11202100467V dated Jul. 8, 2022.
Written Report for corresponding Singapore Application No. 11202100467V dated Jul. 19, 2022.
Wright et al., "Characterization of therapeutic antibodies in the presence of human serum proteins by AU-FDS analytical ultracentrifugation," Anal. Biochem., 2018, vol. 550, pp. 72-83; Available online Apr. 11, 2018.
Oliver M. Lean, "Binding Specificity and Causal Selection in Drug Design," Phil. Sci., 2020, vol. 87, No. 1, pp. 70-90.
Shah et al., "Bio-layer Interferometry for Measuring Kinetics of Protein-protein Interactions and Allosteric Ligand Effects," J. Vis. Exp., 2014; (84), e51383, doi:10.3791/51383, pp. 1-7.

* cited by examiner

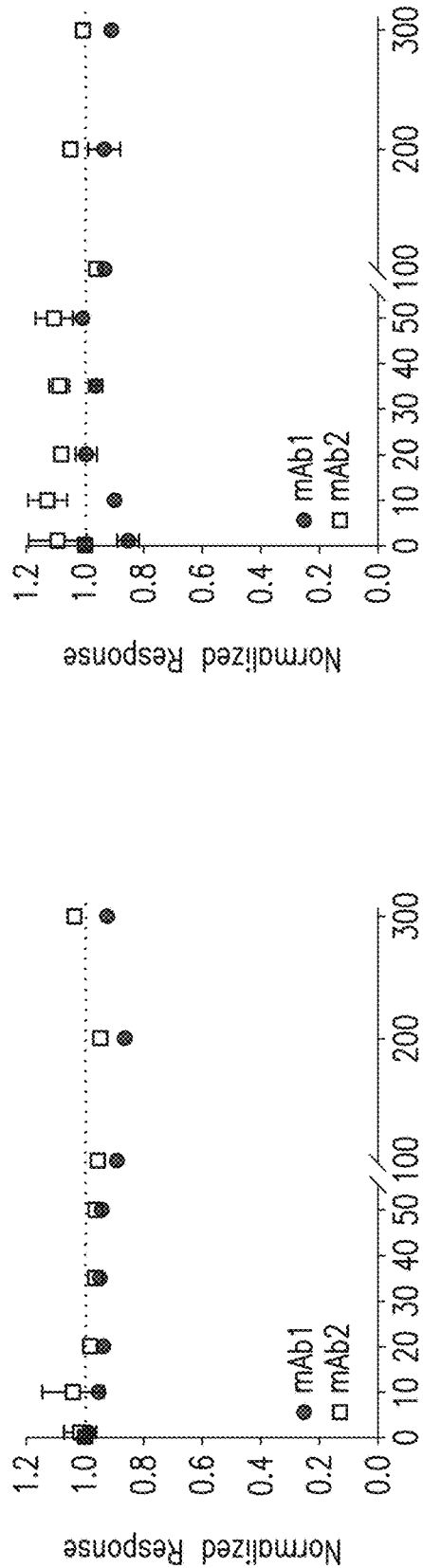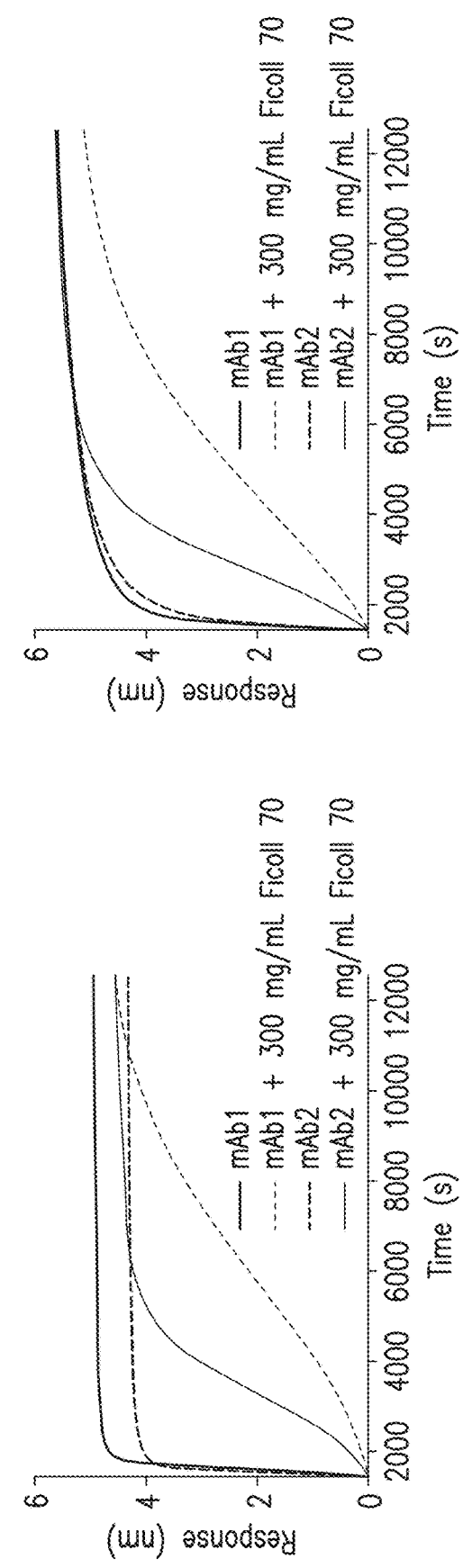

YTE mutation:

FLFPPKPKDTLMISRTPEVTCVVVDVSQEDPEVQFNWYVDGVEVHNAKTK (SEQ ID NO. 1)

FLFPPKPKDTLYITREPEVTCVVVDVSQEDPEVQFNWYVDGVEVHNAKTK (SEQ ID NO. 2)

FIG.17

SEQUENCE LISTING

```
Sequence total quantity: 2
SEQ ID NO: 1           moltype = AA  length = 50
FEATURE                Location/Qualifiers
REGION                 1..50
                       note = Partial Peptide Sequence of Wild-Type IgG1 or IgG4
source                 1..50
                       mol_type = protein
                       organism = synthetic construct
SEQUENCE: 1
FLFPPKPKDT LMISRTPEVT CVVVDVSQED PEVQFNWYVD GVEVHNAKTK          50

SEQ ID NO: 2           moltype = AA  length = 50
FEATURE                Location/Qualifiers
REGION                 1..50
                       note = Partial Peptide Sequence of IgG1 or IgG4 with YTE
                        Mutation
source                 1..50
                       mol_type = protein
                       organism = synthetic construct
SEQUENCE: 2
FLFPPKPKDT LYITREPEVT CVVVDVSQED PEVQFNWYVD GVEVHNAKTK          50
```

THERAPEUTIC PROTEIN SELECTION IN SIMULATED IN VIVO CONDITIONS

CROSS-REFERENCE TO RELATED APPLICATIONS

This application is a continuation of U.S. application Ser. No. 16/537,811, filed on Aug. 12, 2019, which claims the benefit under 35 USC § 119(e) of US Provisional Application Nos.: 62/718,307, filed Aug. 13, 2018; and 62/865,446, filed Jun. 24, 2019, each of which is incorporated herein by reference in its entirety for all purposes.

REFERENCE TO A SEQUENCE LISTING

The instant application contains a Sequence Listing which has been filed electronically in XML format and is hereby incorporated by reference in its entirety. Said XML copy, created on Nov. 9, 2022, is named 070816-01778_SL.xml and is 3,721 bytes in size.

FIELD OF THE INVENTION

The present invention pertains to biopharmaceuticals, and relates to the determination of the behavior of therapeutic biomolecules, such as antibodies, in near physiological conditions.

BACKGROUND

Proper analysis of in vitro binding equilibria is necessarily constrained to concentrations near the dissociation constant, typically on the order of micromolar and below. Under these conditions, proteins behave essentially as ideal molecules and any non-specific interactions can easily be ignored. Increasing the protein concentration to arbitrarily high values leads to macromolecular crowding, where complex formation is no longer linear with respect to protein concentration and the binding equations derived from the law of mass action are better expressed in terms of thermodynamic activity rather than concentration (Neal, B. L., D. Asthagiri and A. M. Lenhoff (1998). "Molecular origins of osmotic second virial coefficients of proteins." Biophys J 75(5): 2469-2477). The magnitude of the activity coefficient depends on the composition of the whole solution; non-ideality arises not only from elevated levels of the protein itself, but also from the presence of non-interacting macromolecules and co-solutes.

An understanding of the non-specific interactions between proteins under non-ideal conditions, which deviate significantly from those commonly employed for in vitro characterization, is vital to achieving a more complete picture of protein function in a biological context. Thus, there presently is a need for methods for determining the effect of non-specific interactions of biological molecules under simulated in vivo conditions.

SUMMARY OF THE INVENTION

In one aspect, the present invention provides a method of determining the effect of non-specific interactions in simulated in vivo conditions, in which the method includes: (a) contacting a solution comprising a biologically relevant molecular crowding agent and a target molecule with a biosensor, wherein the surface of the biosensor comprises a capture molecule that specifically binds the target molecule; (b) allowing the target molecule to bind to the capture molecule; and (c) determining an amount of the target molecule bound to capture molecule using biolayer interferometry.

In some embodiments, the method further includes comparing the amount of the target biomolecule bound to the capture molecule to a control threshold that distinguishes between a target biomolecule having attractive non-specific interactions with the other molecules in the solution and having repulsive non-specific interaction with the other molecules in the solution.

In various embodiments of the method, the control threshold is the amount of binding normalized to an amount of binding in an ideal, dilute, or semi-dilute solution.

In various embodiments of the method, the biologically relevant molecular crowding agent comprises human serum albumin (HSA).

In some embodiments, the human serum albumin is present at a physiologically relevant concentration.

In some embodiments, the human serum albumin is present at a concentration of between about 1 g/L and about 100 g/L.

In some embodiments, the method further includes determining the amount of binding at two or more concentrations of the biologically relevant molecular crowding agent.

In various embodiments of the method, the biologically relevant molecular crowding agent comprises serum and/or plasma.

In some embodiments, the method further includes determining the amount of binding at two or more pHs, for example, to determine a pH dependence of binding.

In some embodiments, the method further includes determining the amount of binding at two or more salt concentrations, for example, to determine a salt dependence of binding.

In various embodiments of the method, the target molecule comprises a monoclonal antibody and the capture molecule comprises an antigen that specifically binds to the monoclonal antibody.

In various embodiments of the method, the target molecule comprises an antigen and the capture molecule comprises a monoclonal antibody that specifically binds to the antigen.

In various embodiments of the method, the target molecule comprises a receptor or ligand binding fragment thereof and the capture molecule comprises a ligand that specifically binds to the receptor or ligand binding fragment thereof.

In various embodiments of the method, the target molecule comprises a ligand and the capture molecule comprises a receptor or ligand binding fragment thereof that specifically binds to the ligand.

In various embodiments of the method, the capture molecule is coupled to the surface of the sensor with a linker.

In various embodiments of the method, the linker comprises biotin and streptavidin or avidin.

In various embodiments of the method, the target molecule comprises an antibody and the capture molecule comprises anti-IgG Fc.

In various embodiments of the method, the anti-IgG Fc is anti-human IgG Fc.

In another aspect, the present invention provides a method of selecting a biomolecule under simulated in vivo conditions, in which the method includes: (a) contacting a solution simulating in vivo conditions with a biosensor, wherein a surface of the biosensor comprises a capture molecule that specifically binds target biomolecules from a set of two or more target biomolecules of interest, and wherein the solution further comprises a biologically relevant molecular crowding agent and a first target biomolecule selected from the set of two or more target biomolecules of interest; (b) allowing the first target biomolecule to bind to the capture molecule; and (c) determining an amount of the first target biomolecule bound to the capture molecule using biolayer interferometry.

In some embodiments, the method further includes: (a) contacting a second solution simulating in vivo conditions with the biosensor, wherein the second solution further comprises the biologically relevant molecular crowding agent and a second target biomolecule selected from the set of two or more biomolecules of interest; (b) allowing the second target biomolecule to bind to the capture molecule; (c) determining an amount of the second target molecule bound to the capture molecule using biolayer interferometry; and (d) comparing the amount of the first biomolecule bound to the capture molecule and the amount of the second biomolecule bound to the capture molecule to identify which of the first biomolecule and the second biomolecule has a greater amount of binding.

In some embodiments, the method further includes comparing the amount of the first and/or second target biomolecule bound to the capture molecule to a control threshold that distinguishes between a target biomolecule having attractive non-specific interactions with the other molecules in the solution and having repulsive non-specific interactions with the other molecules in the solution.

In various embodiments of the method, the threshold is the amount of binding normalized to an amount of binding in an ideal, dilute, or semi-dilute solution.

In various embodiments of the method, the biologically relevant molecular crowding agent comprises human serum albumin (HSA).

In various embodiments of the method, the human serum albumin is present at a physiologically relevant concentration.

In various embodiments of the method, the human serum albumin is present at a concentration of between about 1 g/L and about 100 g/L.

In some embodiments, the method further includes determining the amount of binding at two or more concentrations of the biologically relevant molecular crowding agent.

In various embodiments of the method, the biologically relevant molecular crowding agent comprises serum and/or plasma.

In some embodiments, the method further includes determining the amount of binding at two or more pHs to determine a pH dependence of binding.

In some embodiments, the method further includes determining the amount of binding at two or more salt concentrations to determine a salt dependence of binding.

In various embodiments of the method, the target molecule comprises a monoclonal antibody and the capture molecule comprises an antigen that specifically binds to the monoclonal antibody.

In various embodiments of the method, the target molecule comprises an antigen and the capture molecule comprises a monoclonal antibody that specifically binds to the antigen.

In various embodiments of the method, the target molecule comprises a receptor or ligand binding fragment thereof and the capture molecule comprises a ligand that specifically binds to the receptor or ligand binding fragment thereof.

In various embodiments of the method, the target molecule comprises a ligand and the capture molecule comprises a receptor or ligand binding fragment thereof that specifically binds to the ligand.

In various embodiments of the method, the capture molecule is coupled to the surface of the sensor with a linker.

In various embodiments of the method, the linker comprises biotin and streptavidin or avidin.

In various embodiments of the method, the target molecule comprises an antibody and the capture molecule comprises anti-IgG Fc.

In various embodiments of the method, the anti-IgG Fc is anti-human IgG Fc.

DESCRIPTION OF THE FIGURES

FIGS. 6A-6D are a set of graphs showing the effect of Ficoll 70 on mAb binding to antigen measured by BLI. Binding of mAb1 (●) and mAb2 (□) to biotinylated antigen in the presence of increasing Ficoll 70 concentrations was observed by biolayer interferometry at 10 mM (FIG. 6A) and 137 mM (FIG. 6B) NaCl. The normalized response (to binding at 0.1 g/L Ficoll 70) is plotted as a function of Ficoll 70 concentration. The dotted line in FIGS. 6A and 6B indicates the normal at 1.0, in order to illustrate the relationship of the data points to this line. Experiments were performed in triplicate, and the mean value and standard deviation are shown. One-way ANOVA was performed at each HSA concentration and p-values <0.05 are indicated with an asterisk. All data are summarized in Tables 5-7. Slow binding kinetics required an extension of the time for mAb association to antigen at very high Ficoll 70 concentrations (200 g/L and above, FIGS. 6C and 6D). Binding of mAbs to biotinylated antigen in the presence of 300 g/L Ficoll was observed by biolayer interferometry at 10 mM (FIG. 6C) and 137 mM (FIG. 6D) NaCl. The aligned responses in nm for mAb1 and mAb2 in the absence of Ficoll 70 are shown as a function of time for an extended association time (~3 hours). Addition of 300 g/L Ficoll 70 to mAb1 and mAb2 show comparatively slowed binding kinetics.

FIG. 17 is a sequence alignment of wild type and the YTE mutation.

DETAILED DESCRIPTION OF THE INVENTION

Figure 1:
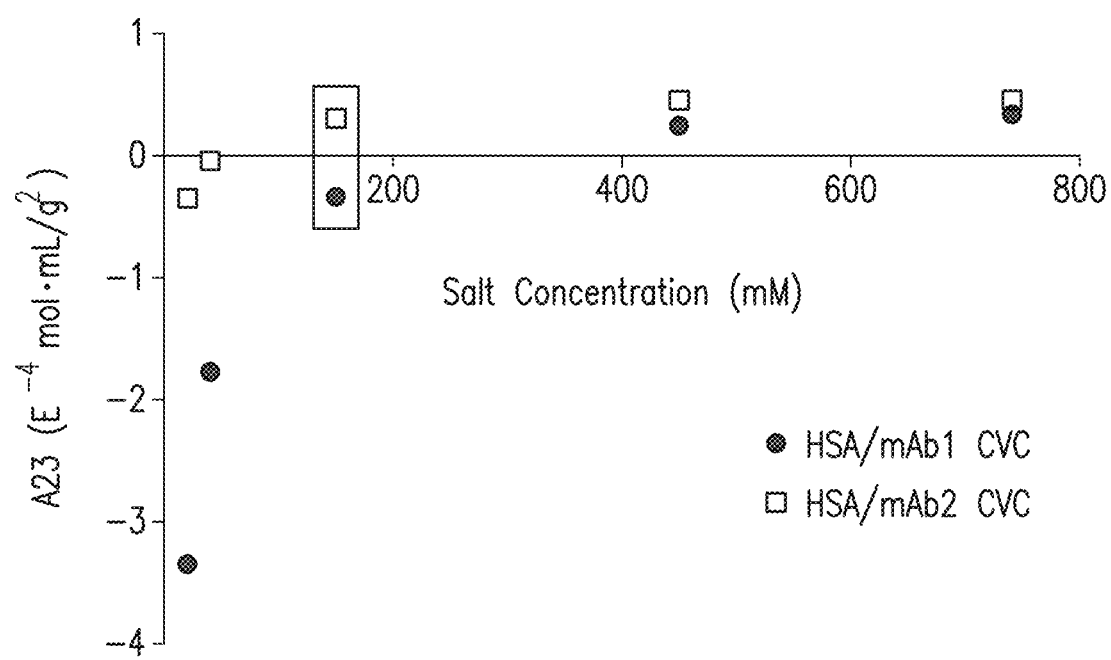
FIG. 1 is a graph showing the ionic strength dependence of mAb1/HSA and mAb2/HSA cross-interactions measured by CG-MALS. Cross-virial coefficients ($A_{23}$) were determined by CG-MALS for interactions between 10 g/L HSA and 10 g/L mAb1 (●) or mAb2 (□) at increasing concentrations of NaCl in phosphate buffer. Negative values for CVC indicate attractive forces between the molecules, while positive CVC values indicate repulsive forces between the molecules. The box indicates physiological ionic strength where the CVC values for mAb1 and mAb2 are negative and positive, respectively.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims. Any embodiments or features of embodiments can be combined with one another, and such combinations are expressly encompassed within the scope of the present invention.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.)

Although any methods and materials similar or equivalent to those described herein can be used in the practice or testing of the present invention, the preferred methods and materials are now described. All patents, applications and non-patent publications mentioned in this specification are incorporated herein by reference in their entireties.

Abbreviations Used Herein

AUC: Analytical Ultracentrifugation
NMR: Nuclear Magnetic Resonance

MALS: Multi-Angle Static Light Scattering

CG-MALS: Composition-Gradient Multi-Angle Light Scattering

HSA: Human Serum Albumin mAbs: Monoclonal Antibodies

BLI: Biolayer Interferometry

SA: Streptavidin

CVC: Cross-Virial Coefficient

MBP: Maltose Binding Protein

FcRn: Neonatal Fc Receptor

FelD1: principal cat allergen

Definitions

The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). In various embodiments, the heavy chain may be an IgG isotype. In some cases, the heavy chain is selected from IgG1, IgG2, IgG3 or IgG4. In some embodiments, the heavy chain is of isotype IgG1 or IgG4, optionally including a chimeric hinge region of isotype IgG1/IgG2 or IgG4/IgG2. Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. For a review on antibody structure, see Lefranc et al., *IMGT unique numbering for immunoglobulin and T cell receptor variable domains and Ig superfamily V-like domains*, 27(1) Dev. Comp. Immunol. 55-77 (2003); and M. Potter, *Structural correlates of immunoglobulin diversity*, 2(1) Surv. Immunol. Res. 27-42 (1983).

The term antibody also encompasses a "bispecific antibody", which includes a heterotetrameric immunoglobulin that can bind to more than one different epitope. One half of the bispecific antibody, which includes a single heavy chain and a single light chain and six CDRs, binds to one antigen or epitope, and the other half of the antibody binds to a different antigen or epitope. In some cases, the bispecific antibody can bind the same antigen, but at different epitopes or non-overlapping epitopes. In some cases, both halves of the bispecific antibody have identical light chains while retaining dual specificity. Bispecific antibodies are described generally in U.S. Patent App. Pub. No. 2010/0331527 (Dec. 30, 2010).

The term "antigen-binding portion" of an antibody (or "antibody fragment"), refers to one or more fragments of an antibody that retain the ability to specifically bind to an antigen. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature 241:544-546), which consists of a VH domain, (vi) an isolated CDR, and (vii) an scFv, which consists of the two domains of the Fv fragment, VL and VH, joined by a synthetic linker to form a single protein chain in which the VL and VH regions pair to form monovalent molecules. Other forms of single chain antibodies, such as diabodies are also encompassed under the term "antibody" (see e.g., Holliger et at. (1993) 90 PNAS U.S.A. 6444-6448; and Poljak et at. (1994) 2 Structure 1121-1123).

Moreover, antibodies and antigen-binding fragments thereof can be obtained using standard recombinant DNA techniques commonly known in the art (see Sambrook et al., 1989).

"Fc fusion proteins" comprise part or all of two or more proteins, one of which is an Fc portion of an immunoglobulin molecule, which are not otherwise found together in nature. Preparation of fusion proteins comprising certain heterologous polypeptides fused to various portions of antibody-derived polypeptides (including the Fc domain) has been described, e.g., by Ashkenazi et at., (1991) 88 Proc. Natl. Acad. Sci. U.S.A. 10535; Byrn et at., (1990) 344 Nature 677; and Hollenbaugh et at., (1992) "Construction of Immunoglobulin Fusion Proteins", in Current Protocols in Immunology, Suppl. 4, pages 10.19.1-10.19.11. "Receptor Fc fusion proteins" comprise one or more extracellular domain(s) of a receptor coupled to an Fc moiety, which in some embodiments comprises a hinge region followed by a CH2 and CH3 domain of an immunoglobulin. In some embodiments, the Fc-fusion protein contains two or more distinct receptor chains that bind to one or more ligand(s). For example, Fc-fusion protein is a trap, such as for example an IL-1 trap (e.g., rilonacept, which contains the IL-1RAcP ligand binding region fused to the IL-1R1 extracellular region fused to Fc of hIgGl; see U.S. Pat. No. 6,927,004), or a VEGF trap (e.g., aflibercept, which contains the Ig domain 2 of the VEGF receptor Flt1 fused to the Ig domain 3 of the VEGF receptor Flk1 fused to Fc of hIgG1; see U.S. Pat. No. 7,087,411 (issued Aug. 8, 2006) and U.S. Pat. No. 7,279,159 (issued Oct. 9, 2007)).

The term "human antibody", is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences. The term includes antibodies recombinantly produced in a non-human mammal, or in cells of a non-human mammal. The term is not intended to include antibodies isolated from or generated in a human subject.

"Bio-layer interferometry" or "BLI" is a label-free technology for measuring biomolecular interactions (see, for example Current Biosensor Technologies in Drug Discovery. Cooper, M. A. Drug Discovery World, 2006, 68-82 and Higher-throughput, label-free, real-time molecular interaction analysis. Rich, R. L.; Myszka, D. G. Analytical Biochemistry, 2007, 361, 1-6). BLI is an optical analytical technique that analyzes the interference pattern of light reflected from two surfaces, for example a layer of immobilized biomolecules on the biosensor tip, and an internal reference layer. A change in the number of target biomolecules bound to the tip of the biosensor causes a shift in the interference pattern that can be measured in real-time.

The binding between a capture molecule immobilized on the biosensor tip surface and a target biomolecule in solution produces an increase in the thickness at the biosensor tip resulting in a wavelength shift. Exemplary instruments for BLI can be obtained commercially, for example from ForteBio, Fremont California.

The term "contacting," as used herein, refers to placement in direct physical association. Contacting can occur in vitro with, e.g., samples, such as biological samples containing a target biomolecule, such as an antibody.

GENERAL DESCRIPTION

With regard to a biological environment, the blood is a complex, crowded solution composed of hundreds of different molecules. An understanding of the non-specific interactions between proteins under such non-ideal conditions, is vital to achieving a more complete picture of protein function in a biological context. Measurement of protein activity in a crowded environment is therefore of utmost importance, and methods such as analytical ultracentrifugation (AUC) and nuclear magnetic resonance (NMR) have been utilized previously to examine molecular behavior in crowded solutions (Heddi, B. & Phan, A. T. Structure of human telomeric DNA in crowded solution. *J Am Chem Soc* 133, 9824-9833, doi:10.1021/ja200786q (2011), Martorell, G., Adrover, M., Kelly, G., Temussi, P. A. & Pastore, A. A natural and readily available crowding agent: NMR studies of proteins in hen egg white. Proteins 79, 1408-1415, doi:10.1002/prot.22967 (2011), Rivas, G., Fernandez, J. A. & Minton, A. P. Direct observation of the self-association of dilute proteins in the presence of inert macromolecules at high concentration via tracer sedimentation equilibrium: theory, experiment, and biological significance. Biochemistry 38, 9379-9388, doi:10.1021/bi990355z (1999), Rivas, G. & Minton, A. P. Non-ideal tracer sedimentation equilibrium: a powerful tool for the characterization of macromolecular interactions in crowded solutions. *Journal of molecular recognition: JMR* 17, 362-367, doi:10.1002/jmr.708 (2004), Pielak, G. J. et al. Protein nuclear magnetic resonance under physiological conditions. *Biochemistry* 48, 226-234, doi: 10.1021/bi8018948 (2009), Wright, R. T., Hayes, D. B., Stafford, W. F., Sherwood, P. J. & Correia, J. J. Characterization of therapeutic antibodies in the presence of human serum proteins by AU-FDS analytical ultracentrifugation. *Analytical biochemistry* 550, 72-83, doi:10.1016/ j.ab.2018.04.002 (2018)). However, these methods present some disadvantages; AUC is a time-consuming method with experiments that can take days, while NMR poses limitations with regard to ionic strength of samples, and consumption of material.

The effects of macromolecular crowding on the thermodynamic and kinetic properties of proteins are remarkably complex and difficult to predict (Elcock, A. H. Prediction of functionally important residues based solely on the computed energetics of protein structure. *J Mol Biol* 312, 885-896, doi:10.1006/jmbi.2001.5009 (2001), Candotti, M. & Orozco, M. The Differential Response of Proteins to Macromolecular Crowding. *PLoS Comput Biol* 12, e1005040, doi:10.1371/journal.pcbi.1005040 (2016), Minton, A. P. The influence of macromolecular crowding and macromolecular confinement on biochemical reactions in physiological media. *The Journal of biological chemistry* 276, 10577-10580, doi:10.1074/jbc.R100005200 (2001), Zimmerman, S. B. & Minton, A. P. Macromolecular crowding: biochemical, biophysical, and physiological consequences. *Annu Rev Biophys Biomol Struct* 22, 27-65, doi:10.1146/annurev.bb.22.060193.000331 (1993)). A principal and unavoidable consequence is steric exclusion, also referred to as the excluded volume effect, which generally leads to a greater potential for macromolecular association in order to increase the volume available for all molecules. The various physicochemical attributes of proteins including size, shape, surface and inherent charge properties, and solvation state contribute to the net non-specific interactions. Furthermore, electrostatic interactions, van der Waals forces, charge anisotropy (local dipole moments), and hydrophobic interactions modulate the overall effect, possibly in opposing manners. Lastly, non-specific interactions depend greatly on solution conditions (e.g., pH and ionic strength; inert co-solutes) and in certain cases may change from net repulsive to attractive interactions (Zhang, Z., Witham, S. & Alexov, E. On the role of electrostatics in protein-protein interactions. *Phys Biol* 8, 035001, doi:10.1088/1478-3975/8/3/ 035001 (2011), Elcock, A. H. & McCammon, J. A. Calculation of weak protein-protein interactions: the pH dependence of the second virial coefficient. *Biophys J* 80, 613-625, doi:10.1016/S0006-3495(01)76042-0 (2001), Blanco, M. A., Perevozchikova, T., Martorana, V., Manno, M. & Roberts, C. J. Protein-protein interactions in dilute to concentrated solutions: alpha-chymotrypsinogen in acidic conditions. *J Phys Chem B* 118, 5817-5831, doi:10.1021/ jp412301h (2014)). Thus, in a solution containing otherwise non-interacting proteins, the non-ideality that stems from high protein concentration may lead to an appreciable level of hetero-association or may maintain the solutes in a more disperse distribution.

The consequences of thermodynamic non-ideality are manifold. From the perspective of antibody manufacturing and formulation, in which the final presentation of the molecule frequently exceeds 100 g/L, non-ideality has been shown to alter a variety of protein solution phenomena, including viscosity, solubility, phase separation, and self-association (Salinas, B. A. et al. Understanding and modulating opalescence and viscosity in a monoclonal antibody formulation. *J Pharm Sci* 99, 82-93, doi:10.1002/jps.21797 (2010), Connolly, B. D. et al. Weak interactions govern the viscosity of concentrated antibody solutions: high-throughput analysis using the diffusion interaction parameter. *Biophys J* 103, 69-78, doi:10.1016/j.bpj.2012.04.047 (2012), Liu, J., Nguyen, M. D., Andya, J. D. & Shire, S. J. Reversible self-association increases the viscosity of a concentrated monoclonal antibody in aqueous solution. *J Pharm Sci* 94, 1928-1940, doi:10.1002/jps.20347 (2005), Raut, A. S. & Kalonia, D. S. Pharmaceutical Perspective on Opalescence and Liquid-Liquid Phase Separation in Protein Solutions. *Mol Pharm* 13, 1431-1444, doi:10.1021/ acs.molpharmaceut.5b00937 (2016)). With respect to specific environments of biological systems including the intracellular milieu, the extracellular matrix, and circulating blood, macromolecular crowding not only impacts binding equilibria, but also reaction rates, protein folding and isomerization, protein-protein interactions, and overall cellular homeostasis (Spitzer, J. From water and ions to crowded biomacromolecules: in vivo structuring of a prokaryotic cell. *Microbiol Mol Biol Rev* 75, 491-506, second page of table of contents, doi:10.1128/MMBR.00010-11

(2011), van den Berg, J., Boersma, A. J. & Poolman, B. Microorganisms maintain crowding homeostasis. *Nat Rev Microbiol* 15, 309-318, doi:10.1038/nrmicro.2017.17 (2017), Zhou, H. X., Rivas, G. & Minton, A. P. Macromolecular crowding and confinement: biochemical, biophysical, and potential physiological consequences. *Annu Rev Biophys* 37, 375-397, doi:10.1146/annurev.biophys.37.032807.125817 (2008). For example, theoretical modeling of cellular osmotic equilibrium, which affects osmotic transport into and out of the cell, requires consideration of non-ideal intracellular thermodynamics due to the crowded cellular environment (Ross-Rodriguez, L. U., Elliott, J. A. & McGann, L. E. Non-ideal solution thermodynamics of cytoplasm. *Biopreserv Biobank* 10, 462-471, doi:10.1089/bio.2012.0027 (2012)). Additionally, macromolecular crowding can influence cellular pathology; accelerated amyloid formation has been demonstrated to occur in crowded environments (Hatters, D. M., Minton, A. P. & Howlett, G. J. Macromolecular crowding accelerates amyloid formation by human apolipoprotein C-II. *The Journal of biological chemistry* 277, 7824-7830, doi:10.1074/jbc.M110429200 (2002), Lashuel, H. A., Hartley, D., Petre, B. M., Walz, T. & Lansbury, P. T., Jr. Neurodegenerative disease: amyloid pores from pathogenic mutations. *Nature* 418, 291, doi:10.1038/418291a (2002), Munishkina, L. A., Cooper, E. M., Uversky, V. N. & Fink, A. L. The effect of macromolecular crowding on protein aggregation and amyloid fibril formation. *Journal of molecular recognition: JMR* 17, 456-464, doi:10.1002/jmr.699 (2004)). The composition of physiological environments often interferes with the analytical methods typically used to characterize virial coefficients. Thus, the phenomenon of thermodynamic non-ideality and the consequences that follow are of both practical and biological significance.

Figure 11:
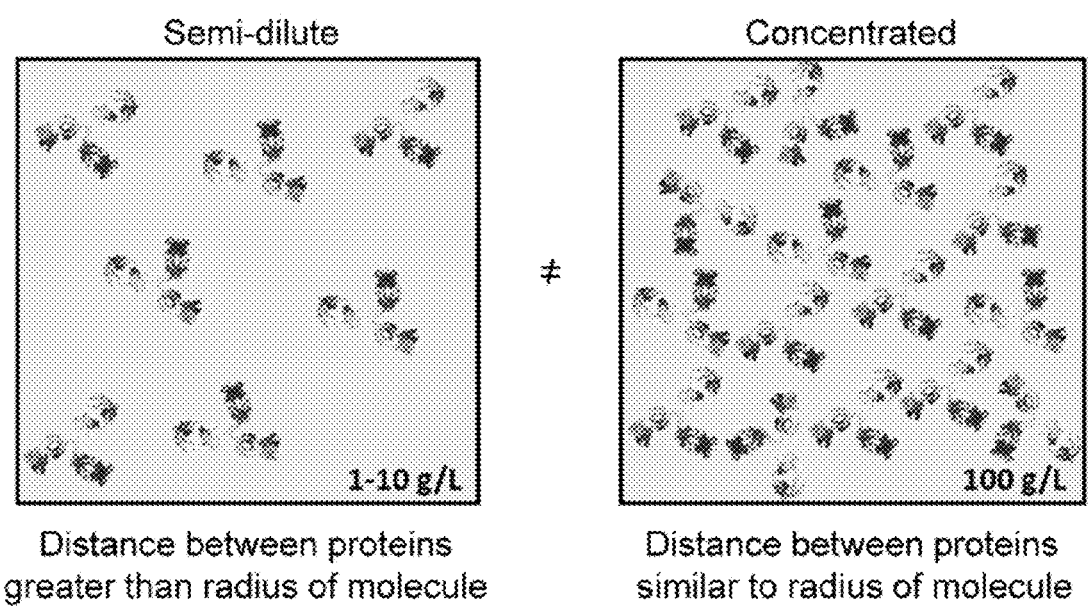
FIG. 11 is a set of schematics demonstrating that semi-dilute solutions are not equivalent to concentrated solutions.

Biotherapeutic proteins, such as monoclonal antibodies, are commonly dosed at high concentrations into the blood, which is an inherently complex and crowded solution with substantial protein content. The effects of macromolecular crowding and the resulting protein non-ideality may lead to an appreciable level of non-specific hetero-association in this physiological landscape (see, FIGS. 11 and 12). Therefore, developing a method to understand non-specific interactions between proteins under such non-ideal, crowded conditions, which deviate significantly from those commonly employed for in vitro characterization, is important to achieving a more complete picture of protein function in a biological context. To this end, the present disclosure pertains to the development of a model system to study the effects of molecular crowding on the interaction of biologically active molecules (e.g., antibodies, bispecific antibodies, fusion proteins, Fc-receptor fusion proteins) and their cognate binding partners, for example antibody-antigen or receptor-ligand interactions. As disclosed herein, by determining the interactions, e.g. binding, of these molecules in a solution that simulates an in vivo environment, information about the behavior of these molecules can be gleaned prior to the initiation of costly in vivo and/or clinical trials. Such information may be used to make informed decisions about what molecules or compounds to pursue as leads for eventual therapeutic agents.

Human serum albumin (HSA) is one of the most abundant proteins in the human circulatory system, making up roughly half the protein content in blood plasma. The relative abundance of HSA and its role in multiple biological processes prompted an examination of its potential interactions with biotherapeutics and, more importantly, how these interactions may affect the biological activity of these biotherapeutics in a subject. Additionally, because albumin is negatively charged at physiological pH this raises possibility of non-specific electrostatic interactions between HSA and biotherapeutics bearing a net positive charge, or large solvent exposed positive surfaces.

Non-specific interactions between human serum albumin (HSA) and two recombinant monoclonal antibodies (mAbs), and the impact of these interactions on mAb:antigen binding, are demonstrated herein. Using biolayer interferometry (BLI), the effect of HSA on antigen binding by mAbs at physiological HSA concentrations was assessed to show that these non-specific interactions have a functional impact on mAb:antigen interactions. Importantly, substitution of Ficoll 70 (an agent used in many molecular crowding experiments) for HSA did not produce similar results, demonstrating that HSA has an effect beyond molecular crowing, for example, due to electrostatic interactions. The presently disclosed in vitro data demonstrates that high concentrations of HSA in the blood serum likely leads to non-specific interactions with mAbs in vivo, with a potential impact on their affinity for antigen as well as with other functionally relevant proteins, including Fc receptors. Taken together, these results demonstrate that BLI based methods disclosed herein can be used to determine the impact of non-specific protein-protein interactions on specific biologically-relevant interactions, providing a direct method to assess binding events in crowded conditions.

Figure 4A:
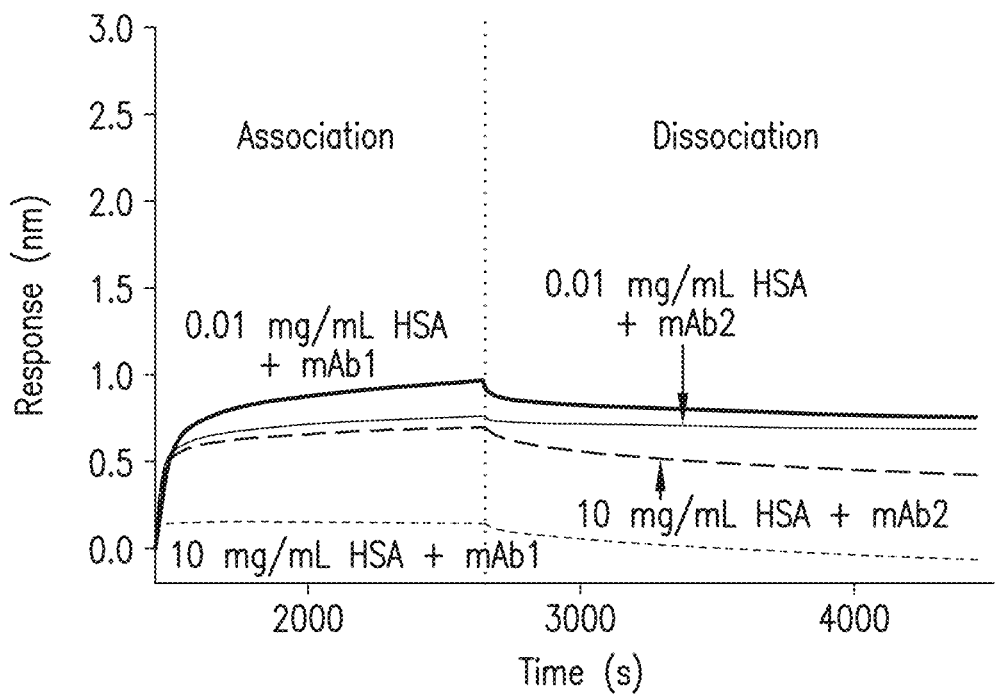
FIGS. 4A and 4B are graphs showing the HSA on mAb binding to antigen measured by BLI is ionic-strength dependent. Binding of 40 nM mAb1 and mAb2 to biotinylated antigen in the absence and presence of HSA was observed by biolayer interferometry at 10 (FIG. 4A) and 137 mM NaCl (FIG. 4B) in phosphate buffer. Change in wavelength (response, nm) as a function of time indicates binding events, and only the mAb association and dissociation steps are shown. Biotinylated antigen was loaded onto SA tips as described above. Binding of mAb1 was assessed in the absence and presence of 10 g/L HSA, and mAb2 binding was assessed in the absence and presence of 10 g/L HSA. A minimum of 0.1 g/L HSA was used to prevent non-specific binding to the biosensor tip. Data traces are aligned at the mAb association step following a baseline measurement in equivalent concentrations of HSA. Traces for samples containing 10 g/L HSA were corrected for a change in signal upon transitioning from association to dissociation due to the change in refractive index of the solution.
Figure 4B:
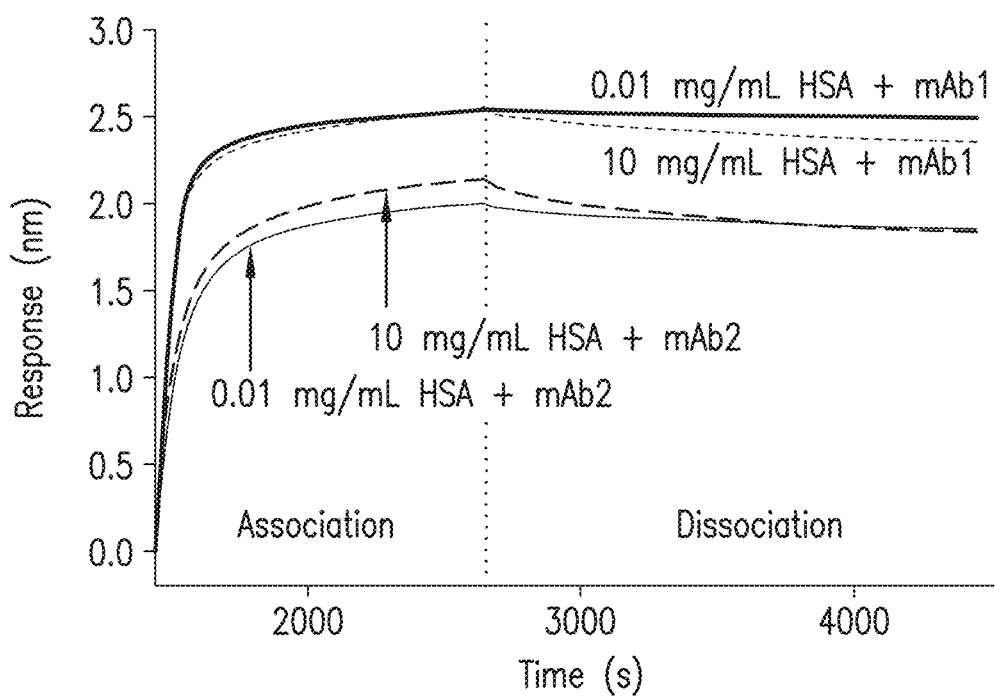

Aspects of the present disclosure relate to a method of determining the effect of non-specific interactions on biomolecule behavior, such as specific binding of an antibody to an antigen and/or epitope thereof, under conditions that simulate in vivo conditions. For example, the methods disclosed herein can be used to predict if a potential therapeutic biomolecule, such as a monoclonal antibody, will be subject to non-specific interactions in vivo that may inhibit its function, such as by reducing the effective concentration, and therefore efficacy, of the potential therapeutic biomolecule. Thus, disclosed herein is a method of assessing the effect of non-specific interactions in simulated in vivo conditions (see FIG. 12 for an exemplary system). In embodiments, the method includes contacting a solution comprising a biologically relevant molecular crowding agent and a target biomolecule with a biosensor. The surface of the biosensor includes a capture molecule that specifically binds the target molecule so that binding of the target biomolecule to the biosensor (mediated through the capture molecule) can be assessed and/or determined. In various embodiments, the biosensor is allowed to incubate in the solution for a time sufficient for the target biomolecule to bind to the capture molecule, for example, when equilibrium is reached. An amount of the target biomolecule bound to the capture molecule is then determined using, e.g., biolayer interferometry (see, for example, FIGS. 4A and 4B). In embodiments, the amount of the target biomolecule bound to the capture molecule is compared to a control, such as a threshold that distinguishes between a target biomolecule having attractive non-specific interactions with the other molecules in the solution and those having repulsive non-specific interactions with the other molecules in the solution. A target biomolecule below the threshold, that is having non-specific attractions, may be less desirable than one above the threshold, which does not exhibit (or which exhibits fewer) such non-specific interactions. Thus, the method can be used to identify target biomolecules that are better suited to in vivo conditions that might be found within a subject administered the identified target biomolecule. In some embodiments, the threshold is a normalized response, for example normalized to a solution that has no or very little molecular crowding agent, and/or an ideal, dilute, or semi-dilute solution. In some embodiments, the biologically relevant molecular crowing agent comprises human serum albumin (HSA) and the amount of binding is normalized to the binding that is observed at a low concentration of HSA, such as between about 0.0001 g/L HSA and 0.1 g/L HSA, for example conditions that are close to or simulate an ideal, dilute, or semi-dilute solution. In this example, the threshold would be set at 1 which corresponds to no net attractive or repulsive forces. A molecule having a normalized response less than 1 may be considered to have non-specific interactions with the biologically relevant molecular crowing agent, such as with HSA, and additional studies to evaluate therapeutic potential may be reconsidered. Conversely, a molecule having a normalized response greater than 1 may be considered devoid of significant non-specific interactions with the biologically relevant molecular crowding agent, such as with HSA, and may be considered to have greater therapeutic potential, which warrants additional evaluation. In embodiments, the HSA is present in the solution at a physiologically relevant concentration. In other embodiments (such as those discussed above or herein in connection with HSA, the molecular crowding agent is selected from IgG, transferrin, fibrinogen, IgA, α2-macroglobulin, IgM, α1-antitrypsin, haptoglobin, α1-acid glycoprotein, apolipoprotein A-1, apolipoprotein A-11, plasma, serum or any other protein components found in blood or serum samples.

In certain embodiments, the HSA is present at a concentration of between about 1 g/L and about 100 g/L, such as about 1, 2, 3, 4, 5, 6, 7, 8, 9, 10, 15, 20, 25, 30, 35, 40, 45, 50, 55, 60, 65, 70, 75, 80, 85, 90, 95, or 100 g/L HSA, for example between about 35-50, 25-40, or 10-80 g/L HSA. In some embodiments, the method is performed at various concentrations of the biologically relevant molecular crowing agent, for example between about 1 g/L and about 100 g/L HSA, for example to determine the response of the target molecule to increasing concentrations of HSA (see, for example, FIGS. 5A and 5B). In embodiments, the method includes determining the amount of binding at two or more concentrations of the molecular crowding agent, for example to create a dose response curve.

In embodiments, the HSA is HSA is loaded with fatty acid (FA), for example to determine an effect of the FA. In some embodiments, the solution includes physiological components (or additional physiological components), such as IgG, transferrin, fibrinogen, IgA, α2-macroglobulin, IgM, α1-antitrypsin, haptoglobin, α1-acid glycoprotein, apolipoprotein A-1, apolipoprotein A-11, or any other protein components found in blood or serum samples. In embodiments, the biologically relevant molecular crowding agent comprises serum and/or plasma.

In embodiments, the solution is at a physiological pH, such as a single physiological pH around neutral pH. However, it is envisioned that the methods can be carried out at a variety of pHs. In certain embodiments, the method further includes determining the amount of binding at two or more pHs to determine a pH dependence of binding.

In embodiments, the solution is at a physiological salt concentration. In certain embodiments, the method further includes determining the amount of binding at two or more salt concentrations to determine a salt dependence of binding.

The disclosed methods can be used to determine the binding of a pair of biologically relevant molecules under conditions that simulate the non-specific interactions of the in vivo environment. In embodiments, the target molecule comprises a monoclonal antibody and the capture molecule comprises an antigen that specifically binds to the monoclonal antibody, for example with high affinity. In embodiments, the target molecule comprises an antigen, such as protein based immunogen and the capture molecule comprises a monoclonal antibody that specifically binds to the antigen. In certain embodiments, the biological target molecule is a set of mutant half-life extension monoclonal antibodies. In certain embodiments, the target molecule comprises a receptor or ligand binding fragment thereof and the capture molecule comprises a ligand that specifically binds to the receptor or ligand binding fragment thereof. In certain embodiments, the target molecule comprises a ligand and the capture molecule comprises a receptor or ligand binding fragment thereof that specifically binds to the ligand.

Aspects of this disclosure further relate to a method of selecting a biomolecule under simulated in vivo conditions. The disclosed method can be used to screen a set of biomolecules, such as a set of potential candidate therapeutic monoclonal antibodies, for additional study, for example in preclinical or clinical trials. In embodiments, the method includes contacting a solution comprising a biologically relevant molecular crowding agent and a target biomolecule (such as a first target biomolecule) with a biosensor. The surface of the biosensor includes a capture molecule that specifically binds the target molecule so that binding of the target biomolecule to the biosensor (mediated through the capture molecule) can be assessed and/or determined. In embodiments, the first target biomolecule is selected from a set of two or more target biomolecules of interest. The biosensor is allowed to incubate in the solution for a time sufficient for the target biomolecule to bind to the capture molecule, for example, when equilibrium is reached. An amount of the target biomolecule bound to the capture molecule is then determined using biolayer interferometry.

In embodiments, the method further includes contacting a solution, such as a second solution simulating in vivo conditions with the biosensor, wherein the second solution includes a second target biomolecule selected from the set of two or more biomolecules of interest. The biosensor is allowed to incubate in the solution for a time sufficient for the second target biomolecule to bind to the capture molecule, for example, when equilibrium is reached. An amount of the second target biomolecule bound to the capture molecule is then determined using biolayer interferometry. In embodiments, the amount of the second biomolecule bound to the capture molecule is compared to the amount of the first biomolecule bound to the capture molecule to identify which of the first biomolecule and the second biomolecule has a greater amount of binding, for example to rank the biomolecules (e.g., antibodies, bispecific antibodies, or fusion proteins) in terms of their respective binding to the capture molecule in a biologically relevant crowding agent. It is contemplated that this process can be repeated for any number of biomolecules in the set of biomolecules of interest, such as a set of monoclonal antibodies of interest. The ranking can be used to select monoclonal antibodies from among the set for further analysis. In certain embodiments, a biomolecule is selected based on in vivo compatibility. In embodiments, the second solution, or third, fourth, etc. is identical to the first solution other than the presence of the individual target biomolecule(s). Thus, the methods disclosed herein can be used to compare the binding of two or more target biomolecules, such as two or more monoclonal antibodies selected from a set of monoclonal antibodies specific for the capture molecule. In embodiments, the amount of the first and/or second target biomolecule bound to the capture molecule may be compared to a control as described above.

In certain embodiments, the biologically relevant crowding agent (e.g., HSA) is present at a concentration of between about 1 g/L and about 100 g/L, such as about, 1, 2, 3, 4, 5, 6, 7, 8, 9, 10, 15, 20, 25, 30, 35, 40, 45, 50, 55, 60, 65, 70, 75, 80, 85, 90, 95, or 100 g/L, for example between about 35-50, 25-40, or 10-80 g/L. In some embodiments, the method is performed at various concentrations of the biologically relevant molecular crowing agent, for example between about 1 g/L and about 100 g/L, for example to determine the response of the target molecules to increasing concentrations of the crowding agent. In embodiments, the method includes determining the amount of binding at two or more concentrations of the molecular crowding agent, for example to create a dose response curve.

In embodiments, the crowding agent is HSA or HSA is loaded with fatty acid (FA), for example to determine an effect of the FA. In embodiments, the solution includes physiological components or additional physiological components, such as IgG, transferrin, fibrinogen, IgA, α2-macroglobulin, IgM, α1-antitrypsin, haptoglobin, α1-acid glycoprotein, apolipoprotein A-1, apolipoprotein A-11, or any other protein components found in blood or serum samples. In embodiments, the biologically relevant molecular crowding agent comprises serum and/or plasma.

In embodiments, the solution is at a physiological pH, such as a single physiological pH around neutral pH. However, it is envisioned that the methods can be carried out at a variety of pHs. In certain embodiments, the method further includes determining the amount of binding at two or more pHs to determine a pH dependence of binding.

In embodiments, the solution is at a physiological salt concentration. In certain embodiments, the method further includes determining the amount of binding at two or more salt concentrations to determine a salt dependence of binding.

Figure 12:
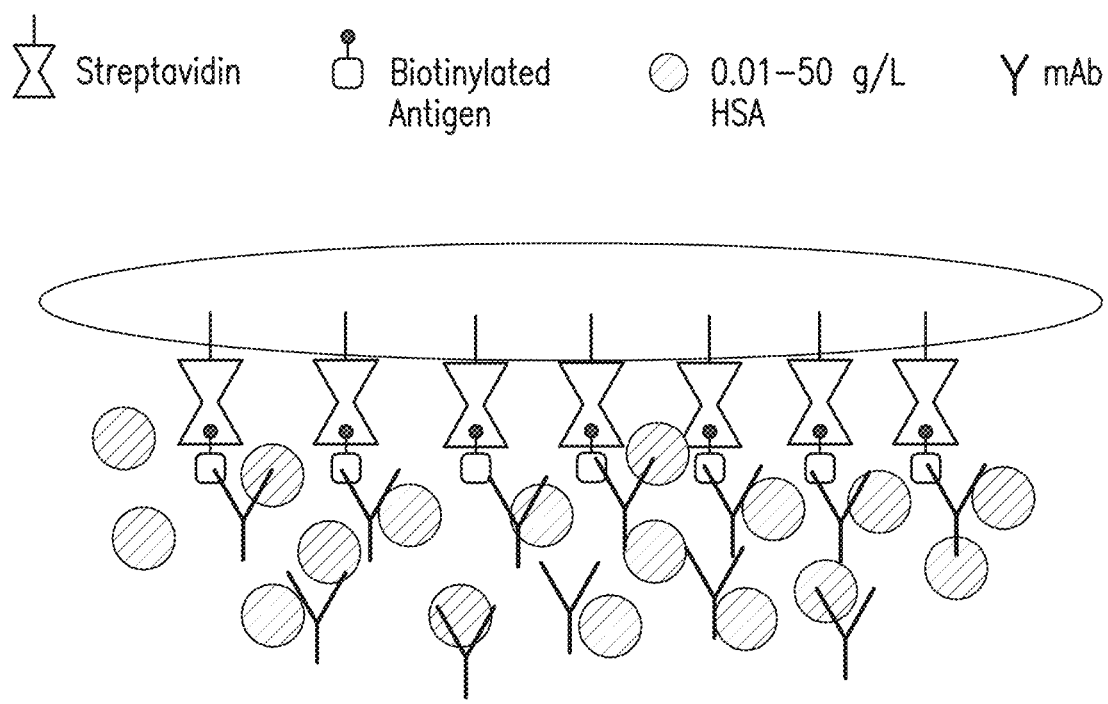
FIG. 12 is a schematic showing a generalized biolayer interferometry system for measuring antibody interactions in the presence of crowding agents and antigen, in accordance with disclosed embodiments.

Capture molecules may be attached to biosensors through any number of means including covalent attachment and/or chemical crosslinking. Target biomolecules may then be attached to the biosensor through specific binding to the capture probe. Manipulation of the biosensors, reagents, and reaction vessels may be performed robotically. The capture of target biomolecules by the biosensor relies on the specific recognition of target molecules, including e.g., specific antibody affinities for antigens. The selected capture molecules are immobilized on a suitable substrate by any method available to one of skill in the art. For example, the capture molecules can be linked directly to a selected functional group on the substrate. Alternatively, the capture molecules can be linked indirectly to the substrate via a linker or spacer. As illustrated in FIG. 12, streptavidin is coupled to the surface of the biosensor and the capture molecule is recruited onto the biosensor through the binding of streptavidin to biotin (biotinylated antigen in the example shown in FIG. 12). In some cases, the selected capture molecule can be immobilized via linkage to streptavidin (or biotin) and then attachment to the substrate via a biotin (or streptavidin) moiety that is covalently linked to the substrate. In certain embodiments, the capture molecule is coupled to the surface of the sensor with a linker. In certain embodiments, the linker comprises biotin and streptavidin or avidin. In an example, the target molecule is an antibody, such as a humanized antibody, and the capture molecule is anti-IgG Fc, such as anti-human IgG Fc.

EXAMPLES

The following examples are put forth so as to provide those of ordinary skill in the art with a complete disclosure and description of how to make and use the methods of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, room temperature is about 25° C., and pressure is at or near atmospheric.

Example 1: Measuring the Effects of Macromolecular Crowding on Protein Function with Biolayer Interferometry Although highly complex at the molecular level, the deviation from ideality that is observed from moderately high levels of protein concentration (on the order of 10 g/L) may be conveniently expressed with the second osmotic virial coefficient (Neal, B. L., Asthagiri, D. & Lenhoff, A. M. Molecular origins of osmotic second virial coefficients of proteins. *Biophys J* 75, 2469-2477, doi:10.1016/S0006-3495 (98)77691-X (1998)). Self ($B_{22}$) and cross ($B_{23}$) virial coefficients characterize weak, non-specific protein-protein interactions in solutions containing single and multiple protein species, respectively. Multi-angle static light scattering (MALS) is a first principles analytical method that allows for the determination of molar mass for a variety of macromolecules, including proteins, in the ideal limit. Static light scattering methods are therefore commonly used to determine the second virial coefficient, which reflects net interactions (protein-protein and protein-solute) and excluded volume effects for all species in solution, from the concentration dependence of molar mass (Alford, J. R., Kendrick, B. S., Carpenter, J. F. & Randolph, T. W. Measurement of the second osmotic virial coefficient for protein solutions exhibiting monomer-dimer equilibrium. *Analytical biochemistry* 377, 128-133, doi:10.1016/j.ab.2008.03.032 (2008)). In composition-gradient multi-angle light scattering (CG-MALS), the light scattering detector is placed downstream of an automated syringe pump system capable of simultaneously injecting up to three different solutions, each containing different molecules, as necessary (Some, D., Kenrick, S. in *Protein Interactions* (ed Jianfeng Cai) (InTech, 2012)). In this batch mode, the weight-average molar mass of all solutes in solution is determined and can provide quantitative analysis of binding interactions with limited prior knowledge. Several implementations of CG-MALS have been developed to characterize specific and non-specific interactions between proteins and other macromolecules. For non-specific protein-protein interactions, the CG-MALS system has the advantage of extracting both self-virial coefficients as well as the cross-virial term from a single experiment. The robustness of the technique, in addition to the well-established analysis algorithm used, enables efficient and relatively straightforward characterization of interactions in protein solutions over a range of concentrations (Some, D., Pollastrini, J. & Cao, S. Characterizing Reversible Protein Association at Moderately High Concentration Via Composition-Gradient Static Light Scattering. *J Pharm Sci* 105, 2310-2318, doi:10.1016/j.xphs.2016.05.018 (2016)).

The CG-MALS method is highly convenient for determining the degree and nature of non-specific interactions between two species; however, the data analysis becomes more cumbersome and less precise for such systems as the concentrations exceed 10 g/L. This led to the pursuit of an alternate method that could extend the concentration range into physiologically relevant concentrations, as well as expand the studies to include the impact of non-specific interactions on specific, functional binding events. Biolayer interferometry (BLI) is a label-free optical technique for measurement of specific macromolecular interactions, including determination of kinetics and binding affinity (Abdiche, Y., Malashock, D., Pinkerton, A. & Pons, J. Determining kinetics and affinities of protein interactions using a parallel real-time label-free biosensor, the Octet®. *Analytical biochemistry* 377, 209-217, doi:10.1016/j.ab.2008.03.035 (2008), Fang, Y., Li, G. & Ferrie, A. M. Non-invasive optical biosensor for assaying endogenous G protein-coupled receptors in adherent cells. *Journal of pharmacological and toxicological methods* 55, 314-322, doi: 10.1016/j.vascn.2006.11.001 (2007), Rich, R. L. & Myszka, D. G. Survey of the year 2006 commercial optical biosensor literature. *Journal of molecular recognition: JMR* 20, 300-366, doi:10.1002/jmr.862 (2007)). BLI analyzes the interference pattern of white light reflected from an internal reference layer as well as a layer of immobilized protein on a biosensor tip (i.e., the biolayer). Binding events increase the number of molecules on the biolayer, producing a shift in the interference pattern which can be monitored in real-time. This method has been used to assess protein-protein interactions (Shah, N. B. & Duncan, T. M. Bio-layer interferometry for measuring kinetics of protein-protein interactions and allosteric ligand effects. *Journal of visualized experiments: JoVE*, e51383, doi:10.3791/51383 (2014)), protein-ligand interactions (Frenzel, D. & Willbold, D. Kinetic titration series with biolayer interferometry. *PloS one* 9, e106882, doi:10.1371/journal.pone.0106882 (2014)), protein-nucleic acid interactions (Park, S. et al. Structural Basis for Interaction of the Tandem Zinc Finger Domains of Human Muscleblind with Cognate RNA from Human Cardiac Troponin T. *Biochemistry* 56, 4154-4168, doi:10.1021/acs.biochem.7b00484 (2017), Sultana, A. & Lee, J. E. Measuring protein-protein and protein-nucleic Acid interactions by biolayer interferometry. *Current protocols in protein science* 79, 19 25 11-26, doi:10.1002/0471140864.ps1925s79 (2015)) and small-molecule and peptide screening (Wartchow, C. A. et al. Biosensor-based small molecule fragment screening with biolayer interferometry. *Journal of computer-aided molecular design* 25, 669-676, doi:10.1007/s10822-011-9439-8 (2011)), among others.

Disclosed herein are methods to measure the impact of non-specific interactions on mAb:antigen interactions in crowded solutions, using human serum albumin (HSA) to demonstrate these principles in a simplified system. Albumin constitutes a significant majority of the volume fraction in serum, at a physiological concentration range of 35-50 g/L, and is negatively charged at physiological pH, which may lead to electrostatic association (or repulsion) with biotherapeutics bearing a net positive (or negative) charge or solvent exposed surface. To this end, non-specific interactions were investigated between HSA and two recombinant fully human IgG4 monoclonal antibodies (mAb1 and mAb2) that bind the same antigen, first in a binary (HSA and mAb) system using CG-MALS, then in a ternary interaction (HSA, mAb, antigen) system with biolayer interferometry (BLI). These mAbs are highly similar in sequence apart from the complementarity-determining region (CDR), which target different epitopes on the antigen. The binary system demonstrated, with well-established light scattering methodologies that non-specific interactions between HSA and mAbs at sub-physiological protein concentrations are both ionic strength-dependent as well as mAb-specific. To further elucidate the effects of these interactions on the functional properties of the mAbs, BLI was utilized in a non-standard manner to assess antigen binding by mAbs from low to physiological HSA concentrations. The BLI results correlated with the CG-MALS data, demonstrating that this novel use of the BLI in the presence of high HSA concentrations can directly assess the impact of non-specific interactions due to crowding on a highly specific, functional interaction such as antibody:antigen binding. The results presented herein demonstrate that high concentrations of HSA in the blood serum leads to non-specific interactions with mAbs, with a potential impact on antibody function. While the effect is particularly apparent at low ionic strength, it is mitigated at physiological ionic strength for this particular set of mAbs; however, this trend does not necessarily extend to all other mAb:antigen systems. By utilizing this approach at an early stage of development of a biotherapeutic, the effects of non-specific interactions can be easily detected; conversely, this type of investigation can also alleviate concern for unanticipated consequences in vivo. Using the BLI platform with an adapted analysis in a simple, controlled system, the inventors demonstrated that the functional impact of non-specific interactions can be determined, setting the stage for exploring the breadth of consequences macromolecular crowding and protein non-ideality may exhibit in more complex solutions.

Materials and reagent preparation: All monoclonal antibodies used in this study were research grade and produced at Regeneron Pharmaceuticals, Inc. in the PreClinical Manufacturing and Process Development Department (Tarrytown, NY). All antibodies are fully human IgG4 molecules and contain the mutation S108P in the hinge region in order to recreate the IgG1 hinge sequence to stabilize IgG4 dimer formation, and were produced in Regeneron's proprietary cell line cloned from Chinese hamster ovary cells. Lyophilized Human Serum Albumin (HSA), Ficoll 70, and solution components were obtained from Sigma-Aldrich (St. Louis, MO) or VWR (Radnor, PA) and were the highest grade available.

Monomeric HSA was prepared by dissolving lyophilized HSA in phosphate buffer (1.8 mM $KH_2PO_4$, 10 mM $Na_2HPO_4$, 2.7 mM KCl, pH 7.4) supplemented with 10 mM NaCl, and purified with a HiLoad 26/100 Superdex 200 size-exclusion column (GE Healthcare Little Chalfont, UK) equilibrated in the same buffer. Following purification, HSA was concentrated to ~100-130 g/L using a centrifugal filter with a 10 kDa cutoff (Amicon, Billerica, MA). The antibodies were prepared in a similar manner for the CG-MALS experiment. HSA concentration was determined with a SoloVPE spectrophotometer at UVA=280 nm using an extinction coefficient of 35,700 $M^{-1}$ $cm^{-1}$. For BLI measurements, the stock solution (1 g/L) of mAb was prepared by diluting a high concentration mAb formulation (>50 g/L) into phosphate buffer supplemented with 10 mM NaCl, and used at a final concentration of 40 nM in equilibrium experiments. Protein concentrations were determined at UVA=280 nm using an extinction coefficient of 103,555 $M^{-1}$ $cm^{-1}$ for mAb1 and 100,700 $M^{-1}$ $cm^{-1}$ for mAb2. The stock solution (600 mM) of Ficoll 70 was prepared by dissolving lyophilized Ficoll 70 into phosphate buffer supplemented with 10 mM NaCl and gently rotated overnight to facilitate solubilization. The antigen was biotinylated with biotin-hydrazide (Thermo Fisher, Waltham, MA) following the manufacturer's labeling protocol.

The glycoprotein antigen was biotinylated on the single glycan with biotin-hydrazide (Thermo Fisher, Waltham, MA) following the manufacturer's labeling protocol. Briefly, a solution of 8 g/L sodium meta-periodate (Sigma-Aldrich) was made using 0.1 M sodium acetate pH 4.7 and mixed with antigen, rotating in foil at room temperature for 15 min, followed by quenching with 1% (v/v) glycerol. Oxidized antigen was eluted through a Superdex 75 Increase 10/300 column (GE Healthcare Little Chalfont, UK) in 0.1 M sodium phosphate pH 6.0. Fractions containing antigen were pooled and concentrated, then incubated with a 10-fold molar excess of biotin-hydrazide for 2 hours at room temperature. Labeled antigen was eluted through the same column equilibrated with phosphate buffer at pH 7.4 supplemented with 10 mM NaCl.

Weak cation exchange chromatography: Weak cation exchange chromatography was performed on a ProPac WCX-10 (4 mm×250 mm) liquid chromatography column (Thermo Fisher) equilibrated with 200 mM MES, 20 mM NaCl, pH 6.5. Proteins were injected neat and 10 μg of each sample was applied to the column on an ACQUITY UPLC system (Waters, Milford, MA) at a flow rate of 0.5 mL/min. A gradient ranging from 20 to 500 mM NaCl was used for protein elution.

Composition Gradient Multi-Angle Light Scattering (CG-MALS): All proteins were dialyzed overnight against the appropriate buffer; all buffers were passed through a 0.02 μm filter and all protein samples were passed through 0.1 μm Anotop 25 Plus syringe filters (Whatman™, Maidstone, UK) and vacuum degassed at ~25 Torr for 10 minutes prior to use. Initial protein stock solutions were manually diluted to approximately 10 g/L prior to filtration. A Calypso® composition gradient system in conjunction with a miniDAWN TREOS MALS photometer and an Optilab® T-rEX™ in-line differential refractometer (Calypso® system and both detectors from Wyatt Technology, Santa Barbara, CA) was employed to collect static light scattering measurements of HSA, mAb, and mixtures thereof using a cross-over gradient scheme. Briefly, the Calypso® pump system was programmed to automatically dilute and inject HSA from 1 to 10 g/L concentrations in 1 g/L increments (10 injections, or steps). Upon injecting undiluted (10 g/L) HSA, the concentration of HSA was reduced by 10% as the concentration of mAb was increased 10% (the cross-over period) in a series of ten injections. After injecting undiluted mAb (10 g/L), its concentration was reduced in 1 g/L increments through a series of nine injections. While this concentration does not reflect physiological conditions, it is the maximum optimal concentration recommended for determination of the cross-virial coefficient. At each step, a 2 mL bolus of appropriately diluted/mixed sample was injected to fully saturate the detector flow cells; data were acquired for 90 seconds under quiescent conditions before creating and injecting a subsequent concentration/mixture step. Baseline measurements were obtained immediately before and after the gradient program. After confirming a lack of significant angular-dependent light scattering, only data from the 90° light scattering detector was used in the analysis. Instrument control, data acquisition, and data analysis (Some, D., Kenrick, S. in *Protein Interactions* (ed Jianfeng Cai) (InTech, 2012), Some, D. Light-scattering-based analysis of biomolecular interactions. *Biophys Rev* 5, 147-158, doi:10.1007/s12551-013-0107-1 (2013)) were all performed with Calypso® software (Wyatt Technology).

Biolayer interferometry: Biolayer interferometry tests were performed using an Octet® Red96 with Streptavidin (SA, cat. number 18-5019) or anti-human IgG Fc capture (AHC, cat. number 18-5064) coated biosensor tips (ForteBio, Menlo Park, CA). The 96-well plates were filled with 200 μL of solution (buffer, antigen, HSA, or mAb) and agitated at 1,000 rpm, and all experiments were temperature controlled at 25° C. Higher temperatures were avoided due to evaporation of solutions. For all tests, SA or anti-human Fc tips were hydrated in phosphate buffer, pH 7.4, supplemented with low (10 mM NaCl) or physiological (137 mM NaCl) salt concentrations for 20 minutes at room temperature. All buffers and sample solutions described contained 0.1 g/L HSA unless otherwise noted. Baseline subtraction was performed with tips dipped into buffer in the absence of analyte.

Standard experiments measuring antigen binding to antibody-loaded tips were performed using AHC tips. Following a baseline measurement of AHC tips in phosphate buffer containing low or physiological salt concentrations supplemented with 0.1 g/L HSA for 2 minutes, the tips were incubated in 2.5 μg/mL antibody to achieve ~0.6 nm response. Antibody-loaded tips were then dipped into buffer to remove excess mAb for 2 min, followed by a 100-300 sec association step with various concentrations of unlabeled antigen, typically 2.5-50 nM. The tips were dipped into buffer for 750 sec for the dissociation step. The same procedure was followed for biotinylated antigen, at 10 mM and 137 mM NaCl, for both mAbs.

Standard binding tests measuring antibody binding to antigen-loaded tips were performed using SA tips. Following a baseline measurement of SA tips in the low or physiological salt phosphate buffer solution containing 0.1 g/L HSA for 2 minutes, the tips were incubated in 5 μg/mL biotinylated antigen to achieve ~0.6 nm response. Antigen-loaded tips were then dipped into buffer to remove excess antigen for 2 min, followed by a 900 sec association step with various concentrations of unlabeled antigen, typically 2.5-50 nM. The tips were dipped into buffer for 1800-3600 sec for the dissociation step. The same procedure was followed for 10 mM and 137 mM NaCl, for both mAbs.

Figure 7:
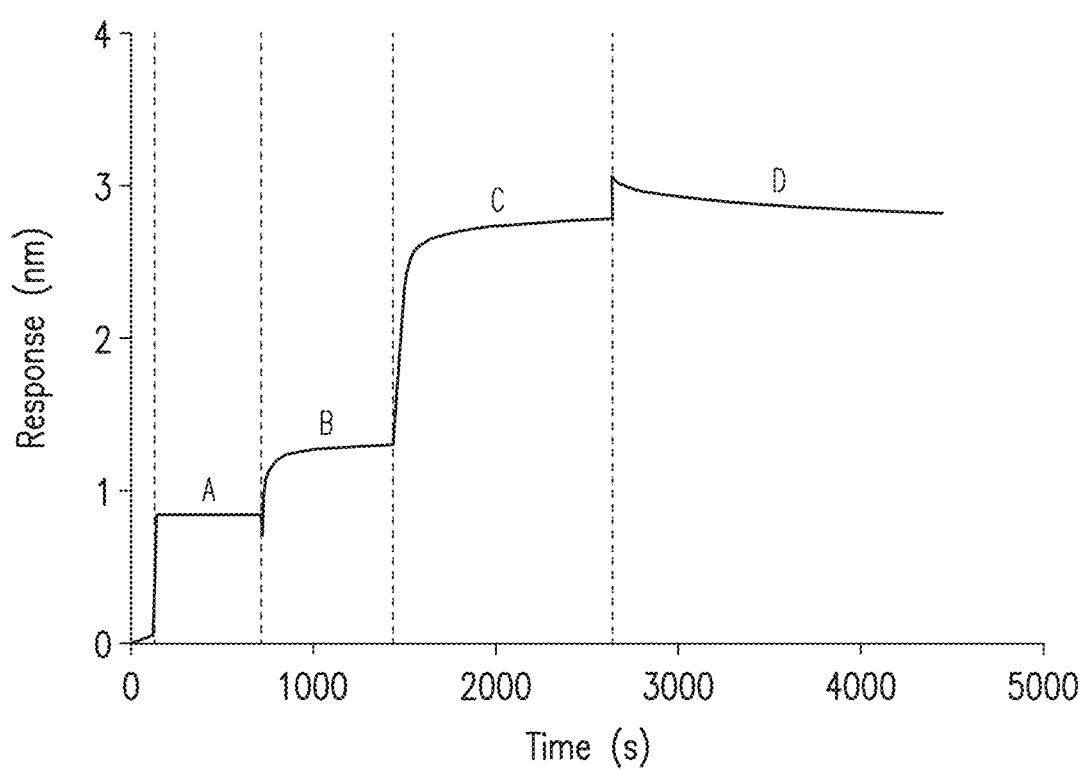
FIG. 7 is a graph showing that biosensor dipping into HSA solution produces an increase in signal in biolayer interferometry experiments. A representative sensorgram for mAb1 binding to an SA tip loaded with biotinylated antigen in 137 mM NaCl. Following a baseline measurement (0-120 s), biotinylated antigen is loaded in the presence of 0.1 g/L HSA and allowed to equilibrate (step A), the sensor dips into 10 g/L HSA (step B), the sensor dips into 10 g/L HSA+40 nM mAb1 (step C), and the sensor dips into baseline buffer (step D). The magnitude of the signal increase observed in step B is similar to the increase in signal observed for the same experimental set-up with biotin-loaded SA (no antigen), indicating the signal is due to refractive index of the high protein concentration of HSA rather than a specific binding event to the biosensor tip (data not shown).
Figure 8A:
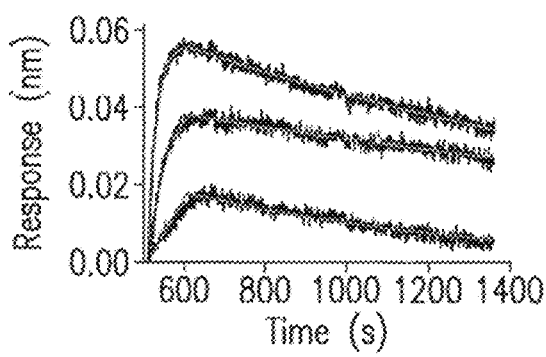
FIGS. 8A-8H are a set of graphs showing affinity measurements with anti-human IgG Fc capture tips. Representative biolayer interferometry sensorgrams are presented for mAb1 with unlabeled antigen in 10 mM (FIG. 8A) and 137 mM NaCl (FIG. 8B); mAb1 with biotinylated antigen in 10 mM (FIG. 8C) and 137 mM NaCl (FIG. 8D); mAb2 with unlabeled antigen in 10 mM (FIG. 8E) and 137 mM NaCl (FIG. 8F); mAb2 with biotinylated antigen in 10 mM (FIG. 8G) and 137 mM NaCl (FIG. 8H). Biosensor tips were loaded with antibody to achieve ~0.6 nm response. Antigen association step was from 100-300 sec and dissociation was 600-750 sec.
Figure 8B:
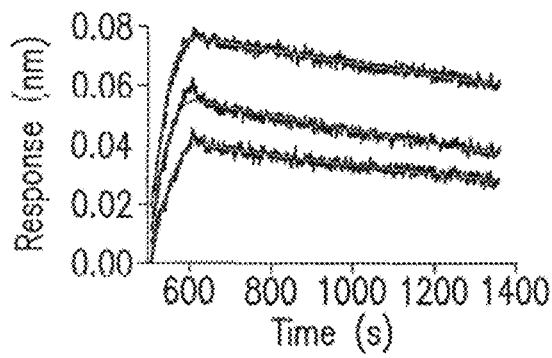
Figure 8C:
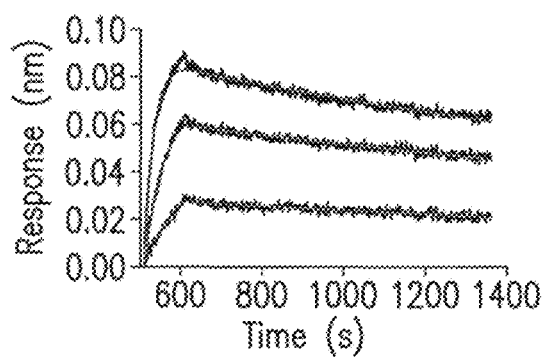
Figure 8D:
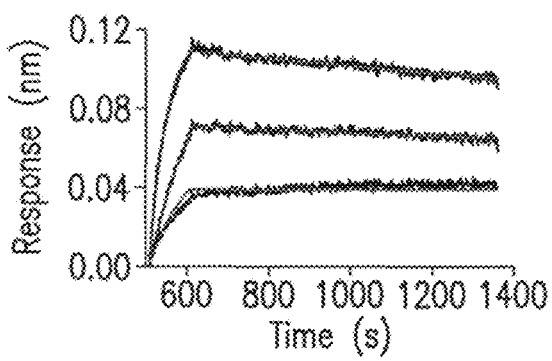
Figure 8E:
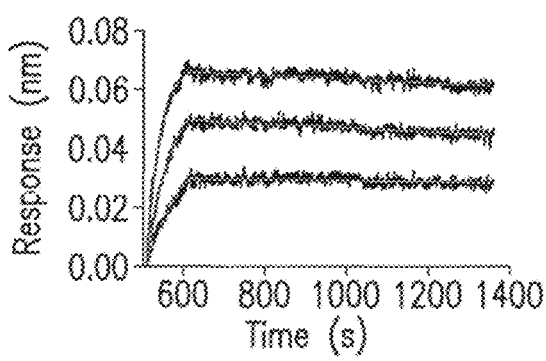
Figure 8F:
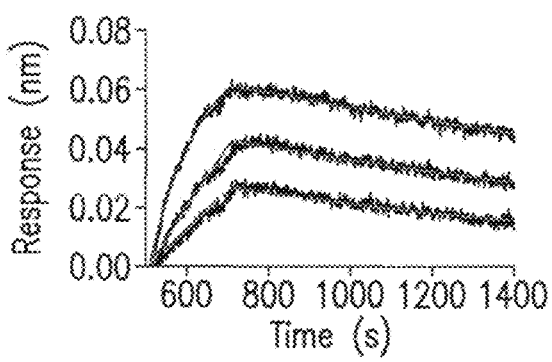
Figure 8G:
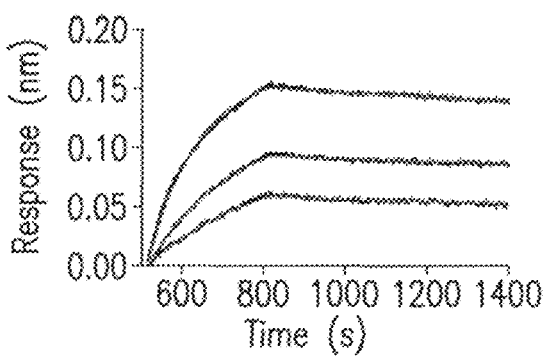
Figure 8H:
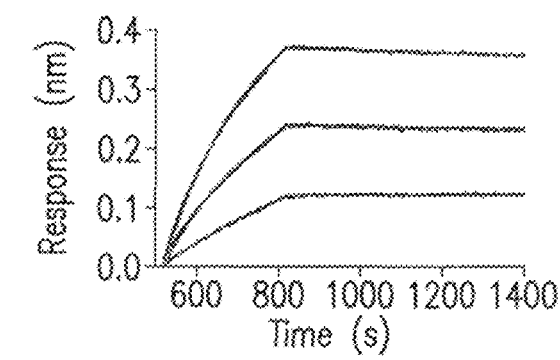

For steady state analysis of mAb binding to antigen in the presence of up 50 g/L HSA, an additional incubation step in HSA was required. Following antigen loading, sensors were dipped into wells containing 0.1-50 g/L HSA for equilibration for ~15 min, followed by a 2 minute incubation in fresh solution with the same composition to establish a new baseline due to a slight increase in signal upon HSA incubation (see FIG. 7, step B). Sensors were then dipped into wells containing 40 nM mAb plus 0.1-50 g/L HSA for 20 minutes as a second association step. For all equilibrium experiments, signal response (nm) at the completion of the mAb binding to antigen association step was used as the metric. No kinetic analysis was performed for any experiments measuring mAb:antigen binding in the presence of HSA >0.1 g/L. The data were normalized to 1.0 by dividing the raw response (in nm) obtained for each HSA concentration by the raw response of mAb:antigen binding in 0.1 g/L HSA. All experiments were performed in triplicate. One-way analysis of variance (ANOVA) was performed using JMP software (SAS Institute, Cary, NC) at each condition to assess whether differences between mAb1 and mAb2 were statistically significant through determination of p-values.

Experiments containing Ficoll 70 were performed in a similar manner, substituting HSA with Ficoll 70. For experiments containing 200 g/L Ficoll 70 or above, a longer association time for mAb binding to antigen was required due to increased viscosity (~1.7-3 hours) in order to achieve equilibrium.

Ionic strength dependence of mAb1/HSA and mAb2/HSA non-specific interactions: Non-specific interactions between HSA and each mAb at different ionic strengths were examined using composition-gradient multi-angle light scattering (CG-MALS), which is a well-established approach to determine the cross-virial coefficient (CVC). This approach was applied to determine both the degree and nature of non-specific interactions between HSA and the mAbs prior to analysis by BLI in order to best interpret the data. Several investigators have pointed out, based on rigorous thermodynamic principles, that the virial coefficient determined from static light scattering is not a pure self, or cross, interaction parameter, but rather it is convolved with protein:co-solute (i.e., buffer or electrolyte) interactions (Alford, J. R., Kendrick, B. S., Carpenter, J. F. & Randolph, T. W. Measurement of the second osmotic virial coefficient for protein solutions exhibiting monomer-dimer equilibrium. *Analytical biochemistry* 377, 128-133, doi:10.1016/j.ab.2008.03.032 (2008), Deszczynski, M., Harding, S. E. & Winzor, D. J. Negative second virial coefficients as predictors of protein crystal growth: evidence from sedimentation equilibrium studies that refutes the designation of those light scattering parameters as osmotic virial coefficients. *Biophys Chem* 120, 106-113, doi:10.1016/j.bpc.2005.10.003 (2006), Winzor, D. J., Deszczynski, M., Harding, S. E. & Wills, P. R. Nonequivalence of second virial coefficients from sedimentation equilibrium and static light scattering studies of protein solutions. *Biophys Chem* 128, 46-55, doi:10.1016/j.bpc.2007.03.001 (2007)). Therefore, the preferred convention is to refer to the virial coefficient from light scattering analysis as $A_2$ in order to distinguish it from the molal condition ($B_{22}$). Provided the proteins are not highly charged and the co-solutes are simple buffers and electrolytes, numerical differences between $A_2$ (used here) and $B_{22}$ are minimal. Similarly, the CVC from light scattering measurements, or $A_{23}$, is an indicator of the nature and degree of non-specific interactions between two species, and was measured for mAb1/HSA and mAb2/HSA interactions in buffered solutions containing 10-750 mM NaCl (FIG. 1). A negative value for $A_{23}$ indicates attractive forces between the two species, while a positive value indicates repulsive forces. At a concentration of 10 mM NaCl, both mAb1/HSA and mAb2/HSA exhibited attractive forces, with stronger forces observed between mAb1/HSA compared to mAb2/HSA. This phenomenon was mitigated with increasing ionic strength. At physiological ionic strength (~137 mM NaCl), the non-specific interactions between mAb1 and HSA were slightly attractive while those between mAb2 and HSA were slightly repulsive. This shows both the ionic-strength dependence and mAb-dependence of non-specific interactions with HSA. To determine the role of electrostatics in these interactions, the molecules were assessed by ion exchange chromatography.

Figure 2:
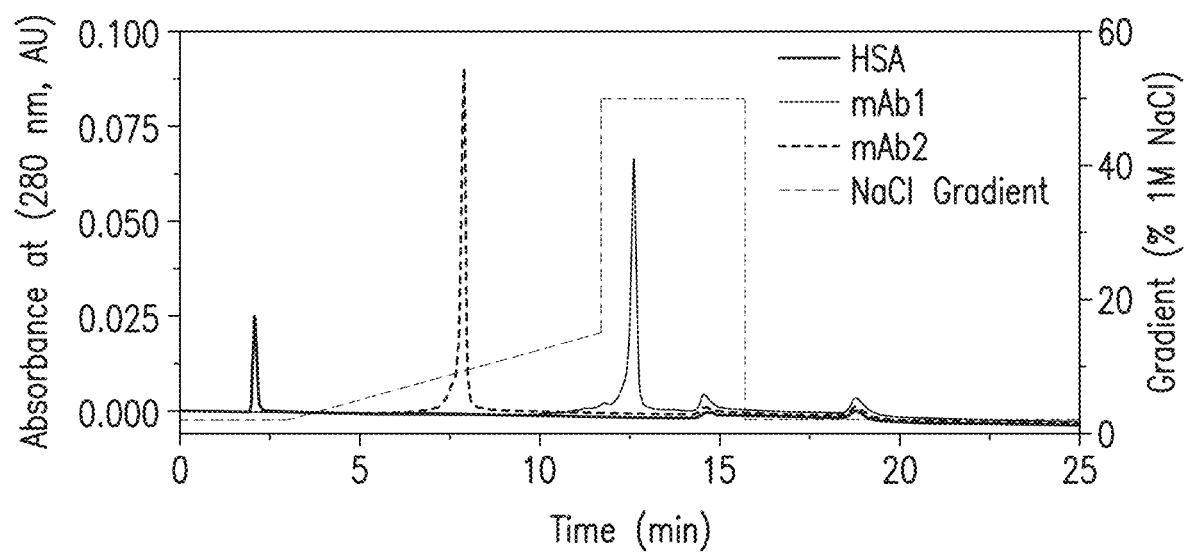
FIG. 2 is a graph showing weak cation exchange chromatography elution profiles for mAbs and HSA. Each mAb and HSA were assessed by analytical chromatography on a weak cation exchange column equilibrated with 200 mM MES, 20 mM NaCl, pH 6.5. A gradient was applied from 20-500 mM NaCl and is represented by a dashed line as a percentage of a 1 M NaCl solution. Representative elution profiles for HSA, mAb1, and mAb2 are shown.

Chromatographic methods show that mAb1 and mAb2 have different surface properties: The surface properties of mAb1 and mAb2 were examined to determine whether the differing degree of non-specific interaction with HSA could be driven by long range charge-charge interactions between the molecules. Subsequently, weak cation exchange chromatography was performed to more specifically assess the surface properties of the two mAbs. These experiments showed that the retention time of mAb1 (~13 min.) was much longer than for mAb2 (~6 min.), indicating stronger interactions with the charged column resin (FIG. 2). Similarly, the chromatographic profile for HSA was assessed, which eluted at a very low retention time (~2 min.) compared to the two mAbs, indicating a more acidic surface charge. Assessment of the mAbs with hydrophobic interaction chromatography showed minimal differences in the elution volume (data not shown), indicating that the differences in non-specific interaction between the mAbs and HSA is likely electrostatic in nature rather than due to a hydrophobic interaction. Together, these data demonstrate that surface properties of each mAb could play a significant role in the degree and nature of the non-specific interactions with HSA. To further assess these interactions, as well as their impact on functional properties of the mAbs, biolayer interferometry was used to examine binding affinity of the mAbs to antigen in the absence and presence of HSA.

The two mAbs bind to biotinylated antigen with a similar binding affinity using biolayer interferometry: In order to assess the effect of physiologically relevant levels of HSA on the binding properties of the two mAbs, biolayer interferometry (BLI) was utilized to monitor association of the mAbs to their common antigen. To test the system and reagents, standard affinity measurement experiments were performed using anti-human IgG Fc capture (AHC) biosensor tips, loading mAb1 or mAb2 onto the tip, and measured antigen binding (FIGS. 8A-8H) with either unmodified antigen or biotinylated antigen in low and physiological salt conditions. The data from these experiments are summarized in Table 1, and show strong similarity to previously generated Biacore surface plasmon resonance (SPR) data (data not shown) with regard to $k_{on}$, $k_{off}$, and $K_D$.

TABLE 1

Binding kinetic parameters from kinetic assays performed by BLI with anti-human Fc capture biosensor tips.

| Biosensor | Ligand | Analyte | Salt | $K_a$ ($\times 10^5$ 1/Ms) | $K_d$ ($\times 10^{-4}$ 1/s) | $K_D$ ($\times 10^{-9}$ M) |
|---|---|---|---|---|---|---|
| AHC | mAb1 | antigen | 10 mM | 12.0 ± 0.2 | 6.0 ± 0.05 | 0.5 ± 0.009 |
| AHC | mAb1 | antigen | 137 mM | 7.2 ± 0.1 | 4.8 ± 0.04 | 0.7 ± 0.01 |
| AHC | mAb1 | Bi-antigen | 10 mM | 9.7 ± 0.07 | 2.0 ± 0.02 | 0.2 ± 0.002 |
| AHC | mAb1 | Bi-antigen | 137 mM | 3.8 ± 0.03 | 2.1 ± 0.02 | 0.6 ± 0.06 |
| AHC | mAb2 | antigen | 10 mM | 4.6 ± 0.04 | 0.9 ± 0.02 | 0.2 ± 0.006 |
| AHC | mAb2 | antigen | 137 mM | 3.0 ± 0.02 | 3.2 ± 0.02 | 1.1 ± 0.09 |
| AHC | mAb2 | Bi-antigen | 10 mM | 3.0 ± 0.01 | 1.3 ± 0.006 | 0.4 ± 0.002 |
| AHC | mAb2 | Bi-antigen | 137 mM | 1.3 ± 0.006 | 5.6 ± 0.005 | 0.4 ± 0.004 |

Figure 3A:
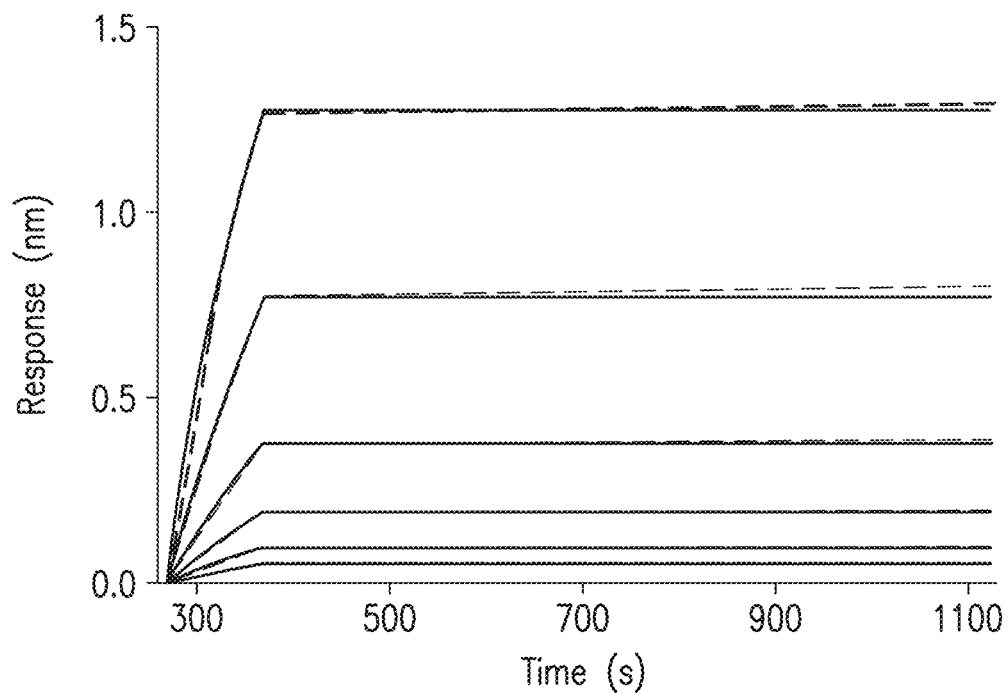
FIGS. 3A and 3B are graphs showing the binding of mAb to biotinylated antigen at 137 mM NaCl in absence of HSA measured by BLI. Binding of mAb1 (FIG. 3A) and mAb2 (FIG. 3B) to biotinylated antigen was observed using biolayer interferometry at physiological salt concentration in phosphate buffer. Change in wavelength in nanometers (response, nm) is plotted as a function of time to indicate changes in thickness of the biolayer due to binding events. Association and dissociation steps are shown for 1.25 nM, 2.5 nM, 5 nM, 10 nM, 20 nM, and 40 nM mAb. Dashed traces indicate raw data and solid traces indicate fitted curves. Data traces are aligned at the mAb association step, and reference data was subtracted from all sample traces.
Figure 3B:
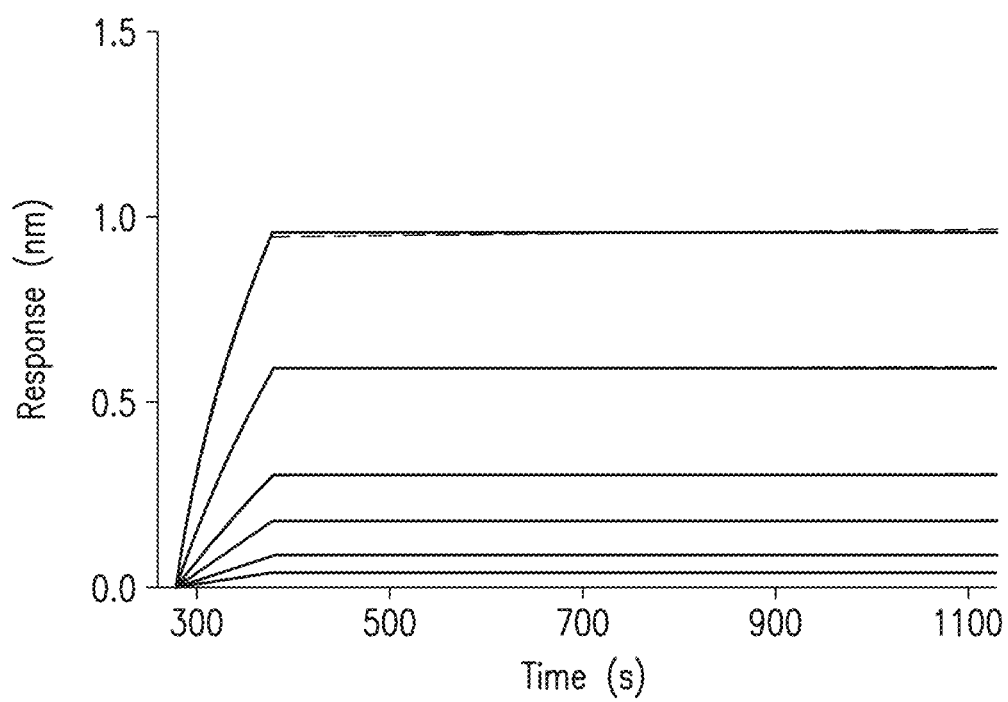

Standard avidity measurement experiments were performed with antigen-loaded biosensor tips to detect antibody binding. To do this, the antigen was site-specifically biotinylated and loaded onto the streptavidin-coated biosensor tip. By immobilizing the smaller antigen rather than the mAb, the change in response (in nm) resulting from binding of antibody gave a more pronounced signal, and thus improved signal to noise. FIG. 3 shows the results from the standard BLI test performed to determine binding affinity for each mAb under ideal solution conditions. The slow dissociation kinetics do not enable an accurate estimate of apparent $K_D$ but the tight binding indicates sub-nanomolar functional binding avidity, which is consistent with Biacore SPR data (not shown).

Having established that the kinetic binding tests performed under ideal solution and experimental conditions produced consistent results to previously performed Biacore SPR studies (data not shown) and that the prepared reagents were fully active, mAb binding to biotinylated antigen was examined in the presence of high, physiologically relevant concentrations of HSA. Due to response level of binding to antigen at a concentration of 40 nM mAb, which allows for monitoring of decreases and increases in signal and is well below the approximate physiological dosing concentration of ~550 nM, this concentration was chosen for all subsequent binding experiments.

The overall effect of HSA on mAb binding to antigen is ionic-strength dependent and mAb-specific: To investigate the effect of HSA on mAb-antigen binding, a BLI test was employed under non-ideal solution conditions and analyzed steady state, end-point data. By monitoring the steady-state response (nm) level after a lengthy (20 min) association step with each mAb, the level of binding to antigen achieved was determined in the presence of HSA at or near equilibrium. Kinetic (on and off-rate) analysis was not performed because of the avidity format and the added complexity imparted by increasing concentrations of HSA. A control was also performed with only HSA in the absence of antibody (data not shown) to demonstrate that HSA does not interact with the antigen. FIG. 4 shows sensorgrams for mAb1 and mAb2 in the presence and absence of 10 g/L HSA at either 10 mM or 137 mM NaCl. These data qualitatively show the difference the effect of HSA has at the two ionic strength conditions for the two mAbs, demonstrating both the ionic-strength dependence and differences in mAb interactions with HSA. At low salt, the effect of HSA is greater on mAb1 than on mAb2, reflected in the difference in response upon addition of HSA. At physiological salt, the impact of 10 g/L HSA is minimal on either mAb interaction with antigen. These results correlate with the CG-MALS data described above, and reveal a potential effect on functional properties of mAbs.

Figure 5A:
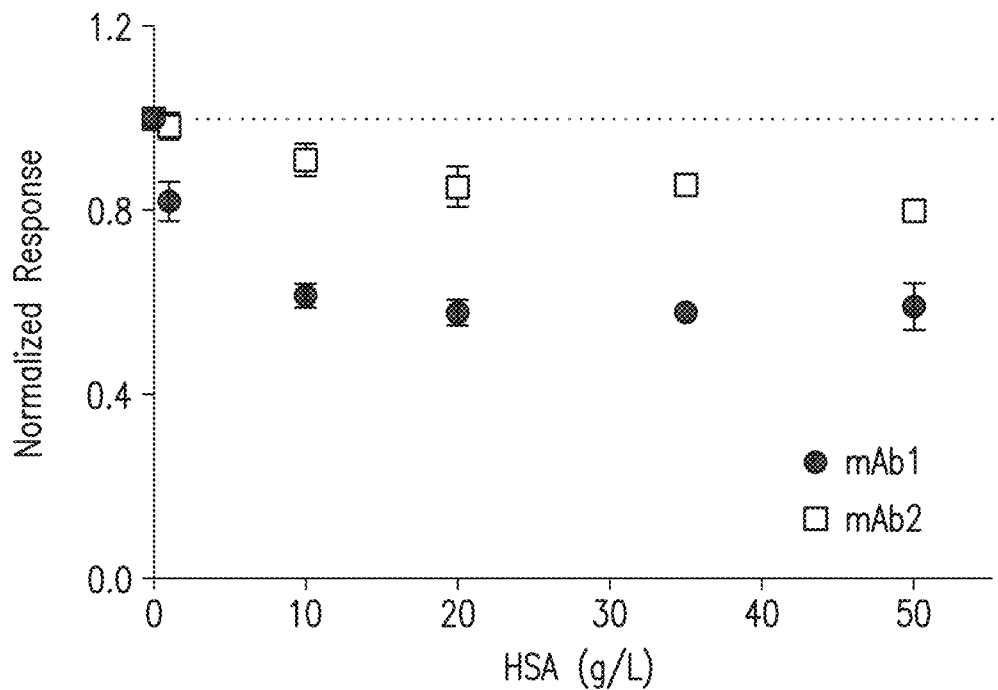
FIGS. 5A and 5B are graphs showing that the effect of HSA on mAb binding to antigen measured by BLI is ionic-strength dependent and mAb-specific. Binding of mAb1 (●) and mAb2 (□) to biotinylated antigen in the presence of increasing HSA concentrations was observed by biolayer interferometry at 10 (FIG. 5A) and 137 (FIG. 5B) mM NaCl. The normalized response (to binding at 0.1 g/L HSA) is shown as a function of HSA concentration. The dotted line indicates the normal at 1.0, in order to illustrate the relationship of the data points to this line. A minimum of 0.1 g/L HSA was used to prevent non-specific binding to the biosensor tip. Experiments were performed in triplicate, and the mean value and standard deviation are shown. One-way ANOVA was performed at each HSA concentration and p-values <0.05 are indicated with an asterisk. All data are summarized in Tables 2-4.
Figure 5B:
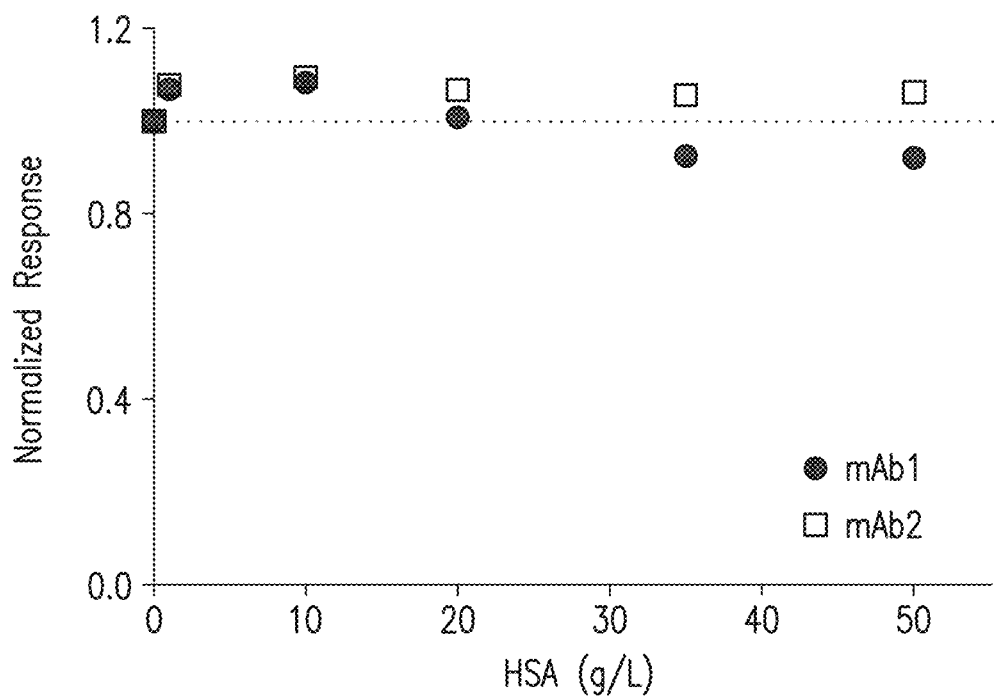
Figure 9:
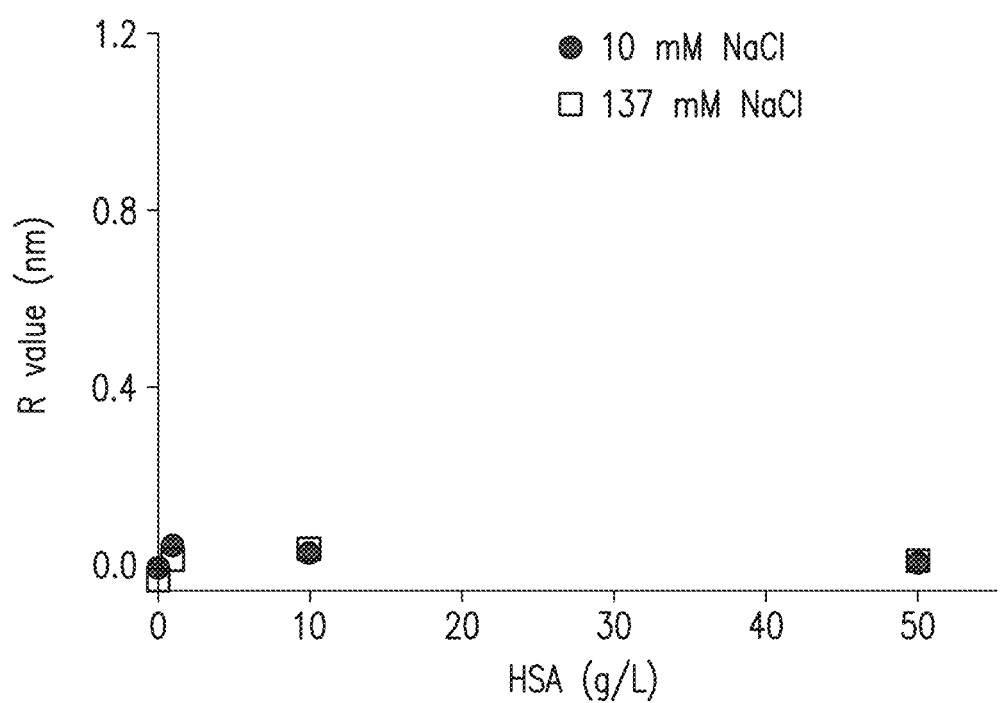
FIG. 9 is a graph showing mAb3 does not bind to antigen and no changes in BLI signal are observed. Binding of mAb3 to biotinylated antigen in the presence of increasing HSA concentrations was observed by biolayer interferometry at 10 (●) and 137 (□) mM NaCl. The observed signal (in nm), rather than the normalized response, is plotted as a function of HSA concentration. Experiments were performed in duplicate, and the mean value and standard deviation are shown.
Figure 10:
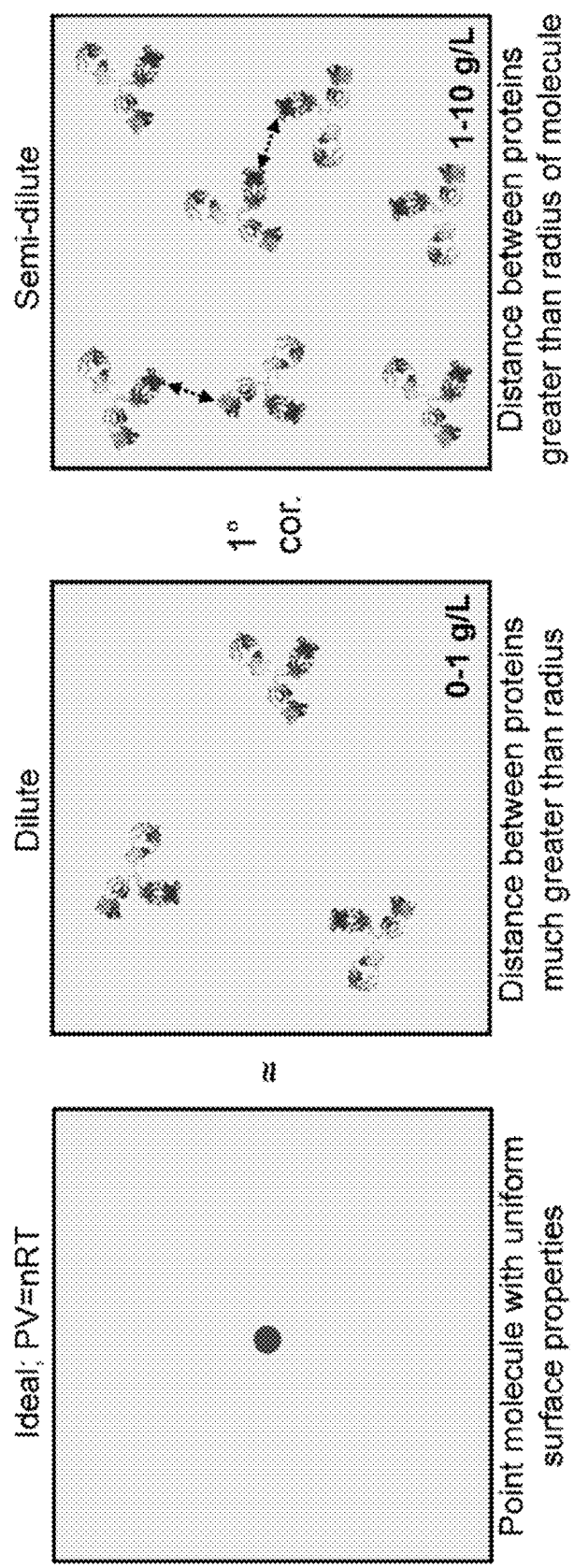
FIG. 10 is a set of schematics demonstrating the difference in ideal, dilute, and semi-dilute solutions.

The effect of increasing HSA concentrations is further illustrated in the low and physiological salt conditions (FIG. 5), where the response level at equilibrium of various HSA concentrations was normalized to the 0.1 g/L HSA level. At 10 mM NaCl, mAb2 had a modest decrease in response (i.e., decrease in antigen binding) with increasing HSA concentrations (~20%), while mAb1 exhibited a more dramatic decrease (~40%; FIG. 5A, Table 2). At 137 mM NaCl, both mAbs showed a modest increase in antigen binding at HSA concentrations under 20 g/L; at higher HSA concentrations, the effect of HSA on antigen binding is greater for mAb1 compared to mAb2 (FIG. 5B, Table 3). In comparison to the response of mAb binding in the absence of HSA (denoted by the dotted line in FIG. 5B), the signal for mAb1 was ~10% reduced while the signal for mAb2 was ~6% enhanced in the physiological HSA range (35-50 g/L, Table 4). The observed binding events were specific to antigen binding; a control mAb (mAb3) that does not bind this antigen showed no increase in signal, or binding, in the presence of 0.1 to 50 g/L HSA (FIG. 9).

TABLE 2

Normalized values for binding response in the presence of HSA in 10 mM NaCl.

| HSA (g/L) | mAb1 Mean | mAb1 Standard Deviation | mAb2 Mean | mAb2 Standard Deviation |
|---|---|---|---|---|
| 0.1 | 1.00 | 0.00 | 1.00 | 0.00 |
| 1.0 | 0.82 | 0.04 | 0.98 | 0.03 |
| 10.0 | 0.62 | 0.03 | 0.91 | 0.04 |
| 20.0 | 0.58 | 0.03 | 0.85 | 0.04 |
| 35.0 | 0.58 | 0.02 | 0.86 | 0.02 |
| 50.0 | 0.59 | 0.05 | 0.80 | 0.01 |

TABLE 3

Normalized values for binding response in the presence of HSA in 137 mM NaCl.

| HSA (g/L) | mAb1 Mean | mAb1 Standard Deviation | mAb2 Mean | mAb2 Standard Deviation |
|---|---|---|---|---|
| 0.1 | 1.00 | 0.00 | 1.00 | 0.00 |
| 1.0 | 1.07 | 0.01 | 1.08 | 0.01 |
| 10.0 | 1.09 | 0.01 | 1.10 | 0.01 |
| 20.0 | 1.01 | 0.01 | 1.07 | 0.02 |
| 35.0 | 0.93 | 0.02 | 1.06 | 0.01 |
| 50.0 | 0.92 | 0.02 | 1.06 | 0.02 |

TABLE 4

Summary of results of ANOVA for mAb1 and mAb2 in HSA.

| HSA (g/L) | Salt concentration (mM) | p-value |
|---|---|---|
| 0.1 | 10 | — |
| 1.0 | 10 | 0.0052* |
| 10.0 | 10 | <.0001* |
| 20.0 | 10 | 0.0009* |
| 35.0 | 10 | <.0001* |
| 50.0 | 10 | 0.0022* |
| 0.1 | 137 | — |
| 1.0 | 137 | 0.1374 |
| 10.0 | 137 | 0.2435 |
| 20.0 | 137 | 0.0035* |
| 35.0 | 137 | 0.0003* |
| 50.0 | 137 | 0.0010* |

*denotes p-value < 0.05

The crowding agent Ficoll 70 does not produce the same effect on mAb binding to antigen: To determine whether the observed effect of HSA on mAb/antigen binding could be attributed to non-specific interactions between mAb and HSA or to a more general macromolecular crowding effect mAb binding to antigen was assessed in the presence of equivalent concentrations of Ficoll 70, a highly soluble polysaccharide frequently used as a crowding agent (Zhou, H. X., Rivas, G. & Minton, A. P. Macromolecular crowding and confinement: biochemical, biophysical, and potential physiological consequences. Annu Rev Biophys 37, 375-397, doi:10.1146/annurev.biophys.37.032807.125817 (2008)). Ficoll 70 is a colorless ~70 kDa polymer that does not interact specifically with proteins. Little to no change was observed in the normalized response of mAb1 and mAb2 binding to antigen at 10 and 137 mM NaCl at concentrations of Ficoll 70 equivalent to those used in HSA experiments (0-50 g/L, FIG. 6). Binding was also assessed at concentrations of Ficoll 70 more representative of those used in crowding studies (100-300 g/L, FIG. 6). As expected, the slow kinetics of mAb binding to antigen in these concentrations of Ficoll 70, particularly for mAb1, required an extension of the association phase to achieve near-equilibrium response levels (overall time was limited to ~3 hours to prevent any evaporation of well solutions; FIGS. 6C and 6D). For both low and physiological salt concentrations, a minimal and highly similar effect on antigen binding was observed for all Ficoll concentrations. These data suggest that the effect on antigen binding observed with HSA is likely due to electrostatic interactions between HSA and the mAb, rather than the more general phenomenon of excluded volume effects.

TABLE 5

Normalized values for binding response in the presence of Ficoll 70 in 10 mM NaCl.

| Ficoll 70 (g/L) | mAb1 | | mAb2 | |
|---|---|---|---|---|
| | Mean | Standard Deviation | Mean | Standard Deviation |
| 0.1 | 1.00 | 0.00 | 1.00 | 0.00 |
| 1.0 | 0.99 | 0.01 | 1.02 | 0.06 |
| 10.0 | 0.96 | 0.01 | 1.04 | 0.11 |
| 20.0 | 0.94 | 0.00 | 0.98 | 0.01 |
| 35.0 | 0.95 | 0.01 | 0.97 | 0.03 |
| 50.0 | 0.94 | 0.01 | 0.96 | 0.00 |
| 100.0 | 0.89 | 0.01 | 0.96 | 0.00 |
| 200.0 | 0.87 | 0.02 | 0.95 | 0.01 |
| 300.0 | 0.93 | 0.02 | 1.04 | 0.01 |

TABLE 6

Normalized values for binding response in the presence of Ficoll 70 in 137 mM NaCl.

| Ficoll 70 (g/L) | mAb1 | | mAb2 | |
|---|---|---|---|---|
| | Mean | Standard Deviation | Mean | Standard Deviation |
| 0.1 | 1.00 | 0.00 | 1.00 | 0.00 |
| 1.0 | 0.86 | 0.04 | 1.10 | 0.10 |
| 10.0 | 0.90 | 0.02 | 1.13 | 0.07 |
| 20.0 | 1.00 | 0.04 | 1.08 | 0.02 |
| 35.0 | 0.97 | 0.02 | 1.09 | 0.03 |
| 50.0 | 1.01 | 0.02 | 1.11 | 0.06 |
| 100.0 | 0.93 | 0.01 | 0.96 | 0.00 |
| 200.0 | 0.94 | 0.05 | 1.05 | 0.01 |
| 300.0 | 0.91 | 0.02 | 1.01 | 0.01 |

TABLE 7

Summary of results of ANOVA for mAb1 and mAb2 in Ficoll.

| Ficoll (g/L) | Salt concentration (mM) | p-value |
|---|---|---|
| 0.1 | 10 | — |
| 1.0 | 10 | 0.5394 |
| 10.0 | 10 | 0.2182 |
| 20.0 | 10 | 0.0010* |
| 35.0 | 10 | 0.1414 |
| 50.0 | 10 | 0.0072* |
| 100.0 | 10 | 0.0009* |
| 200.0 | 10 | 0.0050* |
| 300.0 | 10 | 0.0011* |
| 0.1 | 137 | — |
| 1.0 | 137 | 0.0172* |
| 10.0 | 137 | 0.0046* |
| 20.0 | 137 | 0.0251* |
| 35.0 | 137 | 0.0069* |
| 50.0 | 137 | 0.0674 |
| 100.0 | 137 | 0.0070* |
| 200.0 | 137 | 0.0222* |
| 300.0 | 137 | 0.0011* |

*denotes p-value < 0.05

Macromolecular crowding is ubiquitous in biology. The resulting non-ideal interactions between proteins in crowded solutions are predicted to profoundly affect protein behavior and function (Minton, A. P. The influence of macromolecular crowding and macromolecular confinement on biochemical reactions in physiological media. *The Journal of biological chemistry* 276, 10577-10580, doi:10.1074/jbc.R100005200 (2001), Hu, Z., Jiang, J. & Rajagopalan, R. Effects of macromolecular crowding on biochemical reaction equilibria: a molecular thermodynamic perspective. Biophys J 93, 1464-1473, doi:10.1529/biophysj.107.104646 (2007), Wei, J., Dobnikar, J., Curk, T. & Song, F. The Effect of Attractive Interactions and Macromolecular Crowding on Crystallins Association. *PloS one* 11, e0151159, doi:10.1371/journal.pone.0151159 (2016)). The specific nature of these highly non-linear effects is often difficult to predict, as evidenced by divergent conclusions in several reports (Kuznetsova, I. M., Turoverov, K. K. & Uversky, V. N. What macromolecular crowding can do to a protein. *Int J Mol Sci* 15, 23090-23140, doi:10.3390/ijms151223090 (2014), Minton, A. P. Implications of macromolecular crowding for protein assembly. *Curr Opin Struct Biol* 10, 34-39 (2000)). A limited number of studies using different macromolecular crowding agents have shown considerable consequences for equilibrium constants and reaction rates, often on the order of several logs (Minton, A. P. The influence of macromolecular crowding and macromolecular confinement on biochemical reactions in physiological media. *The Journal of biological chemistry* 276, 10577-10580, doi:10.1074/jbc.R100005200 (2001), Kuznetsova, I. M., Turoverov, K. K. & Uversky, V. N. What macromolecular crowding can do to a protein. *Int J Mol Sci* 15, 23090-23140, doi:10.3390/ijms151223090 (2014), Minton, A. P. Molecular crowding: analysis of effects of high concentrations of inert cosolutes on biochemical equilibria and rates in terms of volume exclusion. *Methods Enzymol* 295, 127-149 (1998), Kim, J. S. & Yethiraj, A. Effect of macromolecular crowding on reaction rates: a computational and theoretical study. *Biophys J* 96, 1333-1340, doi:10.1016/j.bpj.2008.11.030 (2009), Jiao, M., Li, H. T., Chen, J., Minton, A. P. & Liang, Y. Attractive protein-polymer interactions markedly alter the effect of macromolecular crowding on protein association equilibria. *Biophys J* 99, 914-923, doi:10.1016/j.bpj.2010.05.013 (2010)). Together, this highlights the need for techniques capable of readily providing information on the effect of non-ideality in conditions closely replicating physiological environments. Here, it was examined how physiological concentrations of albumin affected monoclonal antibody function with two complimentary techniques, CG-MALS and BLI. CG-MALS, a powerful and well-established tool that enables measurement of the cross-virial coefficient between two species, was used to obtain an initial understanding of non-specific interactions in the systems. A BLI method was then utilized, with steady-state analysis adapted for non-ideal solution conditions, to first replicate the CG-MALS results, and then extend these observations by performing equilibrium measurements of antigen binding under physiological concentrations of HSA. While orthogonal methods such as AUC with fluorescence detection can measure specific interactions in non-ideal conditions (Wright, R. T., Hayes, D. B., Stafford, W. F., Sherwood, P. J. & Correia, J. J. Characterization of therapeutic antibodies in the presence of human serum proteins by AU-FDS analytical ultracentrifugation. *Analytical biochemistry* 550, 72-83, doi:10.1016/j.ab.2018.04.002 (2018), Wright, R. T., Hayes, D., Sherwood, P. J., Stafford, W. F. & Correia, J. J. AUC measurements of diffusion coefficients of monoclonal antibodies in the presence of human serum proteins. *Eur Biophys J*, doi:10.1007/s00249-018-1319-x (2018)), BLI is advantageous as a convenient and high-throughput method to assess binding interactions with inherent flexibility to test many different conditions at high concentrations of crowding agents, and can therefore provide information about binding in various environments in a small set of experiments. This approach is an easy and efficient way to eliminate mAbs or other molecules from consideration during the screening process, early in discovery research.

The physicochemical complexity of the solvent-accessible surface areas presented by different proteins plays a fundamental role in the diversity of non-specific macromolecular interactions. At moderate protein concentrations 10 g/L), where the excluded volume effect is less prominent, electrostatics are likely the dominant intermolecular force (Elcock, A. H. & McCammon, J. A. Calculation of weak protein-protein interactions: the pH dependence of the second virial coefficient. *Biophys J* 80, 613-625, doi:10.1016/S0006-3495(01)76042-0 (2001)). Consistent with this notion, both mAb1 and mAb2, with different experimentally observed basic isoelectric points (differing by ~0.65 pH units), were shown to interact with HSA, possessing an acidic isoelectric point, using CG-MALS. These are not specific interactions, but instead non-specific interactions between HSA and each antibody. For both antibodies, the magnitude of interactions with HSA were shown to be mitigated upon increasing ionic strength, further suggesting the primary force between the molecules is electrostatic, as electrostatic interactions can effectively be screened with increasing ionic strength (Roberts, D. et al. Specific ion and buffer effects on protein-protein interactions of a monoclonal antibody. *Mol Pharm* 12, 179-193, doi:10.1021/mp500533c (2015); Roberts, D. et al. The role of electrostatics in protein-protein interactions of a monoclonal antibody. *Mol Pharm* 11, 2475-2489, doi:10.1021/mp5002334 (2014)). Interestingly, near physiological ionic strength, mAb1 continued to exhibit attractive interactions with HSA while mAb2 exhibited slightly repulsive interactions with HSA. While the two-component system used in CG-MALS does not fully reflect the complexity of physiological conditions and utilizes concentrations below physiological due to technical reasons, the analysis suggests that the degree and nature of non-specific interactions between proteins may impact biological function. As the antibodies differ only in the CDR, it is possible that the difference in the weak interactions with HSA occur at this region. Furthermore, these non-specific interactions are protein-dependent, indicating the potential for a vast spectrum of functional and structural behavior in a physiological environment and possibly explain occasional differences observed between in vitro results and pharmacokinetic and clinical results. Molecular dynamics simulations of synthetic and protein crowders have shown that the effect of crowding on the structure, dynamics, and interactions of proteins within a biological network may facilitate transient interactions that can impact functionality (Candotti, M. & Orozco, M. The Differential Response of Proteins to Macromolecular Crowding. *PLoS Comput Biol* 12, e1005040, doi:10.1371/journal.pcbi.1005040 (2016)). Indeed, it has been hypothesized that evolutionary pressure minimizes non-specific protein-protein interactions to reduce complexity and the potential for protein promiscuity (Johnson, M. E. & Hummer, G. Nonspecific binding limits the number of proteins in a cell and shapes their interaction networks. *Proc Natl Acad Sci USA* 108, 603-608, doi:10.1073/pnas.1010954108 (2011), Deeds, E. J., Ashenberg, O., Gerardin, J. & Shakhnovich, E. I. Robust protein interactions in crowded cellular environments. *Proc Natl Acad Sci USA* 104, 14952-14957, doi:10.1073/pnas.0702766104 (2007)). In addition, several unrelated studies suggest electrostatics are the primary driver of non-specific interactions (Elcock, A. H. Prediction of functionally important residues based solely on the computed energetics of protein structure. *J Mol Biol* 312, 885-896, doi:10.1006/jmbi.2001.5009 (2001), Zhang, Z., Witham, S. & Alexov, E. On the role of electrostatics in protein-protein interactions. *Phys Biol* 8, 035001, doi: 10.1088/1478-3975/8/3/035001 (2011), Gunasekaran, K. et al. Enhancing antibody Fc heterodimer formation through electrostatic steering effects: applications to bispecific molecules and monovalent IgG. *The Journal of biological chemistry* 285, 19637-19646, doi:10.1074/jbc.M110.117382 (2010), Persson, B. A., Jonsson, B. & Lund, M. Enhanced protein steering: cooperative electrostatic and van der Waals forces in antigen-antibody complexes. *J Phys Chem B* 113, 10459-10464, doi:10.1021/jp904541g (2009), Wlodek, S. T., Shen, T. & McCammon, J. A. Electrostatic steering of substrate to acetylcholinesterase: analysis of field fluctuations. *Biopolymers* 53, 265-271, doi:10.1002/(SICI)1097-0282(200003)53:3<265::AID-BIP6>3.0.CO; 2-N (2000)). The CG-MALS and chromatography data presented here further expand on these studies and highlight the importance of understanding surface charge properties of proteins and the potential effects of electrostatic interactions arising from those charges, it is demonstrated herein that non-specific interactions can impact functional interactions such as antibody:antigen binding events.

Utilizing a dip and read design rather than microfluidics, biolayer interferometry is more conducive to studying the impact of non-specific interactions induced by high solute concentrations on highly specific functional interactions, such as antibody:antigen binding. By immobilizing the antigen and using mAb solutions that contained increasing concentrations of HSA, the inventors were able to extend the conditions used for CG-MALS to examine both increased HSA concentration and use the method to establish a ternary interaction system, albeit in an avidity-based format. Importantly, the impact of physiological HSA concentrations on antigen binding was shown to be greater for mAb1 than for mAb2 at low ionic strength, whereas at physiological salt levels, the effect of HSA considerably diminished. Although the magnitude of the difference between the mAbs at physiological ionic strength is considerably less than observed in 10 mM salt, it is statistically meaningful at 20 g/L and above given the precision within the replicates.. While current technical issues with solution evaporation necessitate BLI testing at ambient temperature rather than at physiological temperature, which is in development, this clearly suggests the BLI approach described here is capable of replicating and expanding on the data from light-scattering methods, which were also performed at ambient temperature due to technical issues. Moreover, the non-specific interactions observed with CG-MALS at low ionic strength indeed have a functional impact on antibody:antigen interactions and this effect appears to plateau at moderate HSA concentration; for example, 50 g/L HSA does not have an appreciably larger impact on binding than 35 g/L. It remains unclear if this is a general trend for most therapeutic mAbs or other biotherapeutics and continued investigation is needed. A study performed using the biosensor platform KinExA that tested mAbs associating with their native unpurified antigens in serum (Bee, C., Abdiche, Y. N., Pons, J. & Rajpal, A. Determining the binding affinity of therapeutic monoclonal antibodies towards their native unpurified antigens in human serum. *PloS one* 8, e80501, doi:10.1371/journal.pone.0080501 (2013)) demonstrated that some mAbs show the same apparent affinity in buffer or serum, while others show differences in apparent affinity. These results further our understanding of macromolecular crowding mediated by protein co-solutes. Several proteins including lysozyme, RNase A, albumin, and reconstituted *E. coli* cytosol have been used as macromolecular crowding agents, often with contrasting results. For example, the self-association of apo-myoglobin was found to be enhanced in crowded RNase A solutions, but not in crowded HSA solutions (Zorrilla, S., Rivas, G., Acuna, A. U. & Lillo, M. P. Protein self-association in crowded protein solutions: a time-resolved fluorescence polarization study. *Protein Sci* 13, 2960-2969, doi:10.1110/ps.04809404 (2004)). Conversely, dimerization of the A34F mutant of GB1 was enhanced with 100 g/L BSA and diminished in 50 g/L lysozyme (Kyne, C. & Crowley, P. B. Short Arginine Motifs Drive Protein Stickiness in the *Escherichia coli* Cytoplasm. *Biochemistry* 56, 5026-5032, doi:10.1021/acs.biochem.7b00731 (2017)). The authors point to the differences in charge state, relative to that of A34F, as the principal driver of the observed differences in dissociation constants. Furthermore, weak hetero-interactions in concentrated BSA/SH3 domain solutions slowed the translational diffusion of both proteins well beyond that expected for the solution viscosity (Rothe, M. et al. Transient binding accounts for apparent violation of the generalized Stokes-Einstein relation in crowded protein solutions. *Phys Chem Chem Phys* 18, 18006-18014, doi:10.1039/c6cp01056c (2016)). This likely stems from transient binding events on a timescale comparable or faster than translational diffusion. Taken together with the results presented here, it is clear that transient interactions can have an effect on high affinity (nM-pM) interactions, such as antibody: antigen binding events, as well.

Synthetic polymers such as PEG, dextran, or Ficoll, are frequently used as crowding agents; however, the aim of the investigation is typically protein folding or stability (Candotti, M. & Orozco, M. The Differential Response of Proteins to Macromolecular Crowding. *PLoS Comput Biol* 12, e1005040, doi:10.1371/journal.pcbi.1005040 (2016), McGuffee, S. R. & Elcock, A. H. Diffusion, crowding & protein stability in a dynamic molecular model of the bacterial cytoplasm. *PLoS Comput Biol* 6, e1000694, doi:10.1371/journal.pcbi.1000694 (2010), Mittal, S. & Singh, L. R. Denatured state structural property determines protein stabilization by macromolecular crowding: a thermodynamic and structural approach. *PloS one* 8, e78936, doi: 10.1371/journal.pone.0078936 (2013), Zhou, H. X. Polymer crowders and protein crowders act similarly on protein folding stability. *FEBS Lett* 587, 394-397, doi:10.1016/j.febslet.2013.01.030 (2013), Batra, J., Xu, K., Qin, S. & Zhou, H. X. Effect of macromolecular crowding on protein binding stability: modest stabilization and significant biological consequences. *Biophys J* 97, 906-911, doi:10.1016/j.bpj.2009.05.032 (2009), Senske, M. et al. Protein stabilization by macromolecular crowding through enthalpy rather than entropy. *J Am Chem Soc* 136, 9036-9041, doi:10.1021/ja503205y (2014), Hong, J. & Gierasch, L. M. Macromolecular crowding remodels the energy landscape of a protein by favoring a more compact unfolded state. *J Am Chem Soc* 132, 10445-10452, doi:10.1021/ja103166y (2010)). Relatively few studies have been published on the effects polymers have on heterogeneous protein-protein interactions (Candotti, M. & Orozco, M. The Differential Response of Proteins to Macromolecular Crowding. *PLoS Comput Biol* 12, e1005040, doi:10.1371/journal.pcbi.1005040 (2016), Jiao, M., Li, H. T., Chen, J., Minton, A. P. & Liang, Y. Attractive protein-polymer interactions markedly alter the effect of macromolecular crowding on protein association equilibria. *Biophys J* 99, 914-923, doi:10.1016/j.bpj.2010.05.013 (2010), Phillip, Y. & Schreiber, G. Formation of protein complexes in crowded environments—from in vitro to in vivo. *FEBS Lett* 587, 1046-1052, doi: 10.1016/j.febslet.2013.01.007 (2013), Kozer, N., Kuttner, Y. Y., Haran, G. & Schreiber, G. Protein-protein association in polymer solutions: from dilute to semidilute to concentrated. *Biophys J* 92, 2139-2149, doi:10.1529/biophysj.106.097717 (2007)). Here again, there is no clear consensus regarding the true effects of synthetic polymers and it appears the net outcome is specific to the system of interest. Schreiber and colleagues showed minimal effects of PEG and dextran on interactions between barnase and barstar or between β-lactamase with its protein inhibitor, while Liang and co-workers showed considerable effects of polymer crowding on catalase-superoxide dismutase association (Jiao, M., Li, H. T., Chen, J., Minton, A. P. & Liang, Y. Attractive protein-polymer interactions markedly alter the effect of macromolecular crowding on protein association equilibria. *Biophys J* 99, 914-923, doi:10.1016/j.bpj.2010.05.013 (2010), Phillip, Y., Sherman, E., Haran, G. & Schreiber, G. Common crowding agents have only a small effect on protein-protein interactions. *Biophys J* 97, 875-885, doi:10.1016/j.bpj.2009.05.026 (2009)). Although the impact of high HSA concentration on antibody:antigen binding could simply be due to excluded volume effects, equivalent experiments performed in the presence of the polysaccharide Ficoll 70 rather than HSA yielded different results, showing little to no effect on binding even at high concentrations. The difference is particularly apparent at low ionic strength, which showed a significant mAb-specific decrease in binding activity in the presence of HSA. In Ficoll crowded solutions, the effect is minimal and similar for the two mAbs. This suggests that the effect of HSA cannot be explained purely by effects on excluded volume; the complexity of biological systems (i.e., the surface properties of proteins) plays a significant role in biological processes. Investigations with additional systems of interest are likely to help refine the model of protein macromolecular crowding.

Not surprisingly, high Ficoll concentrations (100 g/L and above) slowed the apparent binding for both antibodies, as assessed by the time required to achieve a steady state condition; however, the effect was more pronounced on mAb1 than mAb2. This suggests an additional protein-specific effect on the binding properties of the system at Ficoll concentrations similar to those used for typical crowding studies in addition to the high solution viscosity. The specific reason for the different effects of high Ficoll concentration on the two mAbs is unclear, but could be attributed to differences in preferential interactions, either binding or exclusion (Arakawa, T. & Timasheff, S. N. Preferential interactions of proteins with solvent components in aqueous amino acid solutions. *Arch Biochem Biophys* 224, 169-177 (1983), Timasheff, S. N. Protein-solvent preferential interactions, protein hydration, and the modulation of biochemical reactions by solvent components. *Proc Natl Acad Sci USA* 99, 9721-9726, doi:10.1073/pnas.122225399 (2002)). Notably, the effects of Ficoll on each mAb were fairly consistent between low and high ionic strength. Previous studies suggest that Ficoll can variably affect the thermal stability and conformational dynamics of molecules (Qu, Y. & Bolen, D. W. Efficacy of macromolecular crowding in forcing proteins to fold. *Biophys Chem* 101-102, 155-165 (2002), Sasahara, K., McPhie, P. & Minton, A. P. Effect of dextran on protein stability and conformation attributed to macromolecular crowding. *J Mol Biol* 326, 1227-1237 (2003), Stagg, L., Zhang, S. Q., Cheung, M. S. & Wittung-Stafshede, P. Molecular crowding enhances native structure and stability of alpha/beta protein flavodoxin. *Proc Natl Acad Sci USA* 104, 18976-18981, doi:10.1073/pnas.0705127104 (2007), Tokuriki, N. et al. Protein folding by the effects of macromolecular crowding. *Protein Sci* 13, 125-133, doi:10.1110/ps.03288104 (2004)), and differences in the CDRs between the two mAbs could contribute to varied Ficoll-induced effects on structure or dynamics, with a concomitant effect on binding. An investigation using maltose binding protein (MBP) showed that Ficoll can bind to the protein and compete with binding of the natural ligand, maltose (Miklos, A. C., Sumpter, M. & Zhou, H. X. Competitive interactions of ligands and macromolecular crowders with maltose binding protein. *PloS one* 8, e74969, doi:10.1371/journal.pone.0074969 (2013)). This demonstrates a direct effect of crowding agents on protein-ligand interactions and the potential consequences of competition from other macromolecules. However, the effects observed with Ficoll were based on the time required to reach equilibrium, rather than on the equilibrium response itself, which demonstrates that polymer (Ficoll) and protein (HSA) crowding agents do not necessarily generate the same result. These potential differences are likely to be dependent on the inherent physicochemical properties associated with the molecules being examined. An additional investigation is necessary to develop a better understanding of this complex phenomenon; furthermore, protein hydration or preferential exclusion/interaction studies may clarify the mechanism behind this discrepancy. Polymer crowders do not consistently produce an effect on ligand binding. Substitution of a protein crowder for the polymers in this system might have a profoundly different effect on the thermodynamics, as this would introduce additional complexity with electrostatic interactions and other non-ideal behavior.

The complexity and volume occupancy of biological solutions impose significant deviations from ideal behavior on constituent molecules. An understanding of the non-ideal behavior and non-specific interactions of proteins under such conditions is vital to achieving a more complete and accurate picture of protein function. Here, the inventors have demonstrated a high-throughput approach to characterize the functional impact of non-specific protein-protein interactions using biolayer interferometry, which allows for screening a large number of test articles in a relatively short time using minimal material. Specifically, the inventors investigated the impact that physiological concentrations of albumin have on antibody-antigen binding. Two different antibodies that bind the same antigen, were affected differently by the presence of albumin, suggesting that biotherapeutics may exhibit a range of non-specific interactions in defined systems with albumin. Assessment of mAb binding to other biologically relevant molecules, such as neonatal Fc receptor (FcRn), in the presence of HSA is paramount. Recycling of both IgG and HSA to the bloodstream from acidic endosomes is facilitated by FcRn in a pH-dependent manner (Vaughn, D. E. & Bjorkman, P. J. Structural basis of pH-dependent antibody binding by the neonatal Fc receptor. *Structure* 6, 63-73 (1998)), and while this process is well-understood, the potential interplay between IgG and HSA that was observed suggests a more complex process (Wang, W. et al. Monoclonal antibodies with identical Fc sequences can bind to FcRn differentially with pharmacokinetic consequences. Drug Metab Dispos 39, 1469-1477, doi:10.1124/dmd.111.039453 (2011)). Lastly, as a largely unexplored area of biotherapeutic development, characterizing non-specific interactions relevant to the indication and route of administration could serve as an important discriminator among a pool of lead candidate molecules. The application of biolayer interferometry technology to a variety of biological and drug discovery problems is expanding (Verzijl, D., Riedl, T., Parren, P. & Gerritsen, A. F. A novel label-free cell-based assay technology using biolayer interferometry. *Biosens Bioelectron* 87, 388-395, doi:10.1016/j.bios.2016.08.095 (2017), Kaminski, T., Gunnarsson, A. & Geschwindner, S. Harnessing the Versatility of Optical Biosensors for Target-Based Small-Molecule Drug Discovery. *ACS Sens* 2, 10-15, doi:10.1021/acssensors.6b00735 (2017), Yang, D., Singh, A., Wu, H. & Kroe-Barrett, R. Determination of High-affinity Antibody-antigen Binding Kinetics Using Four Biosensor Platforms. *Journal of visualized experiments: JoVE*, doi:10.3791/55659 (2017)). As an early discovery research screening tool, BLI can be used to more quickly eliminate candidates from the pipeline, and can be beneficial in diversifying the types of assays used in discovery research. The approach described here is an important tool that can be used in conjunction with other biophysical methods, such NMR and AUC, to better investigate crowded solution phenomena.

Example 2: Selection of Antibodies from the FcRn-Mediated Recycling Pathway

Figure 13:
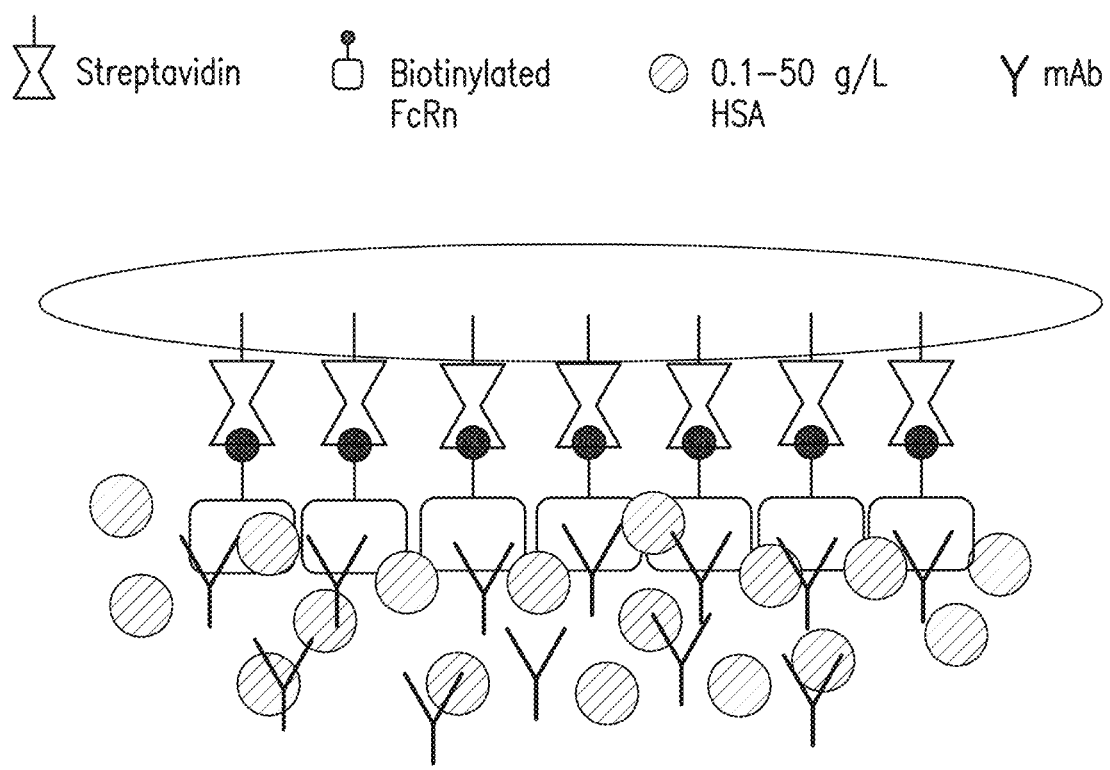
FIG. 13 is a schematic showing a generalized biolayer interferometry system for measuring antibody interactions in the presence of crowding agents and FcRn, in accordance with disclosed embodiments.
Figure 14:
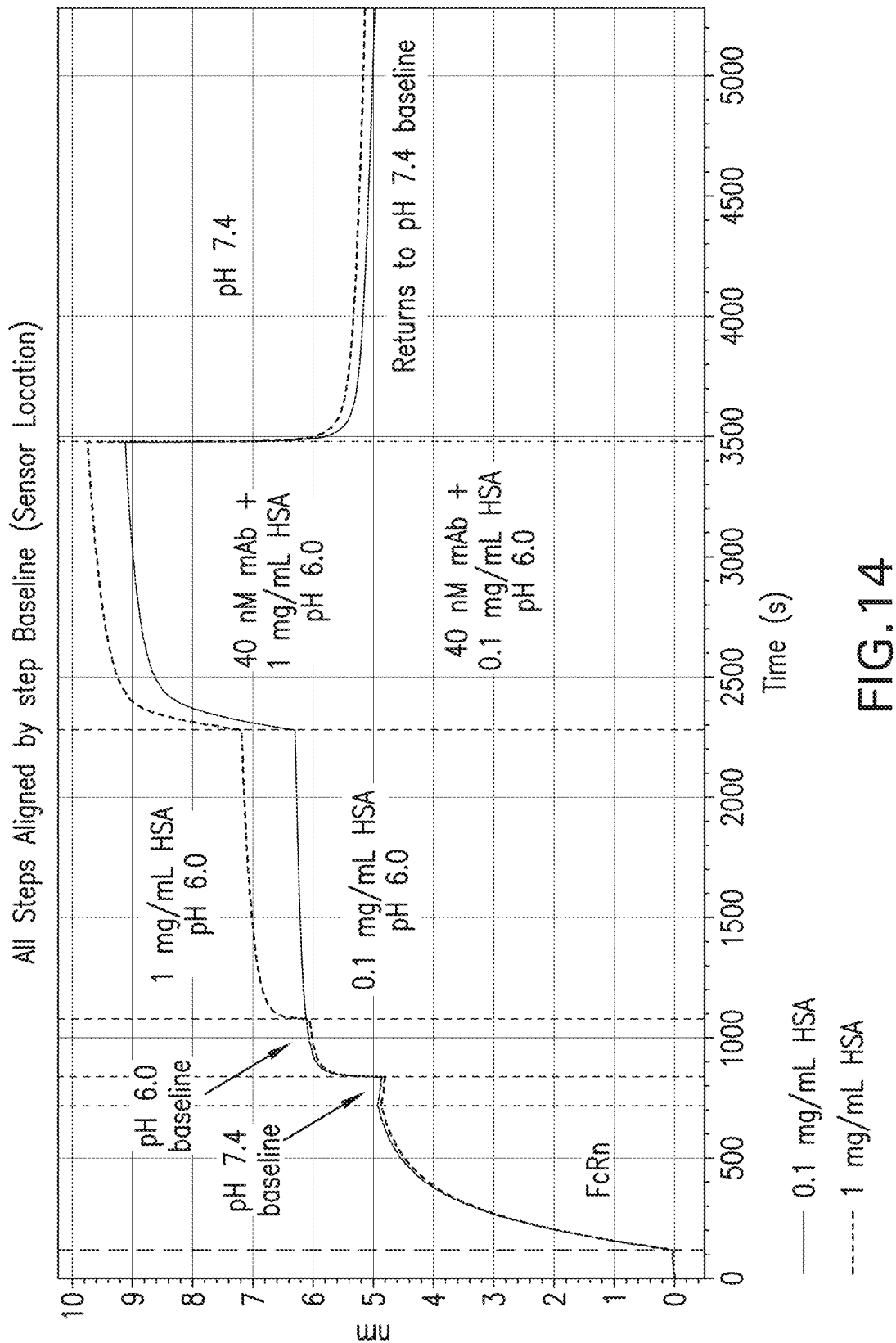
FIG. 14 is graph showing the effects of HSA on antibody/FcRn binding.
Figure 15A:
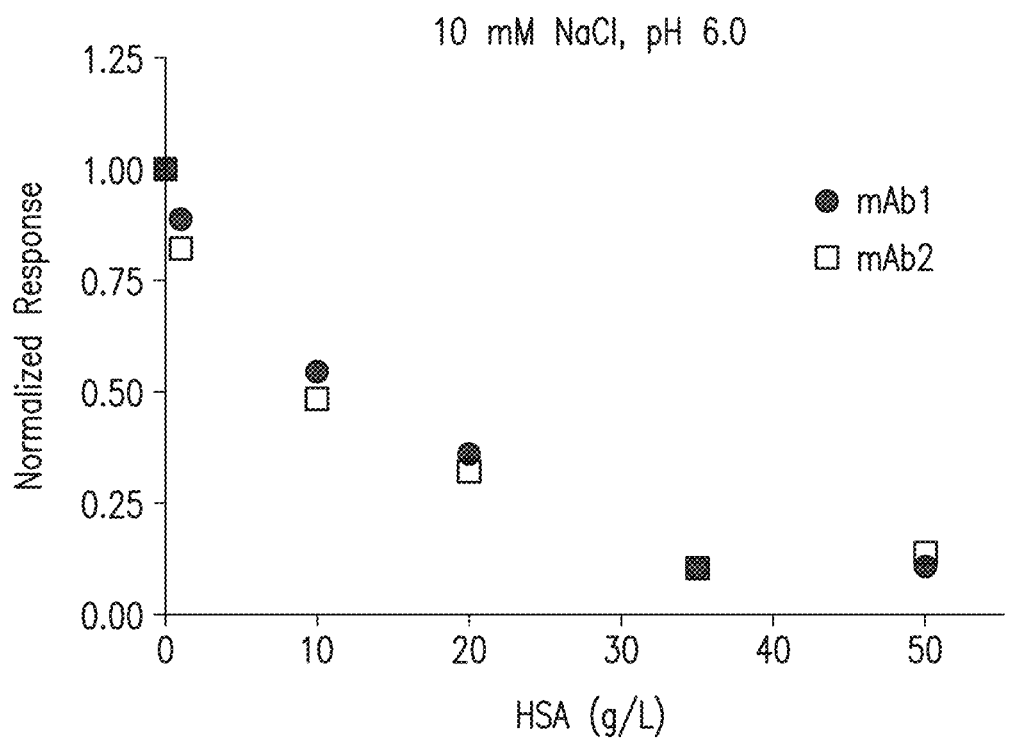
FIGS. 15A and 15B are graphs showing the dose-response curve effects of HSA at different salt concentrations.
Figure 15B:
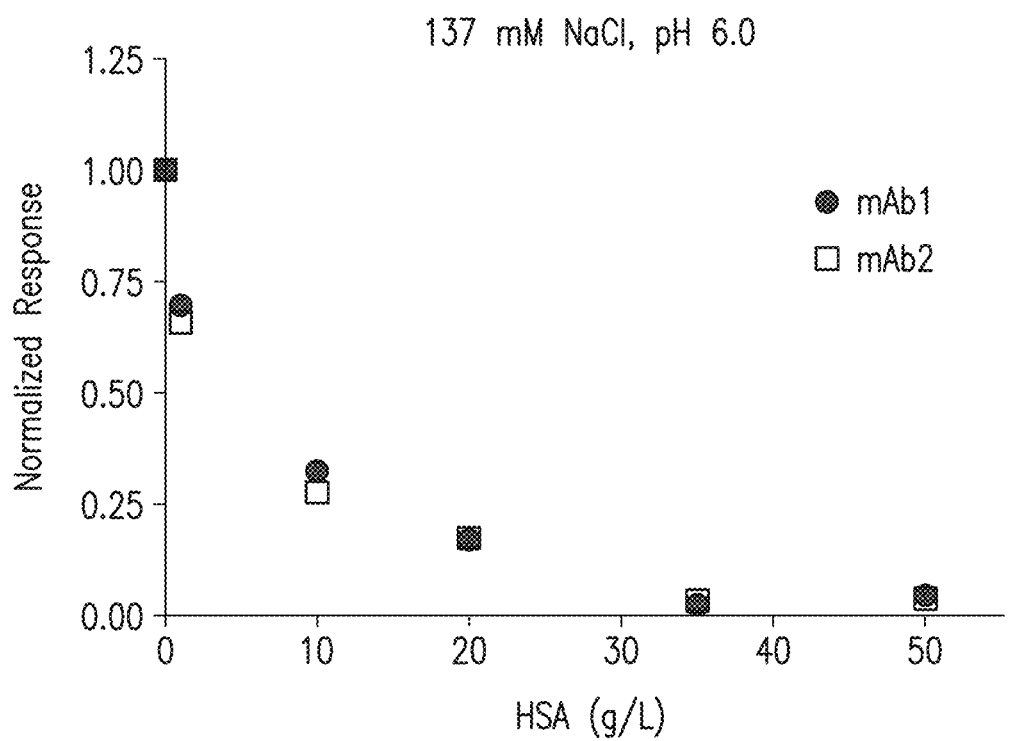

FcRn extends the half-life of IgG and serum albumin by reducing lysosomal degradation in endothelial cells. IgG, serum albumin and other serum proteins are continuously internalized through pinocytosis. Generally, serum proteins are transported from the endosomes to the lysosome, where they are degraded. IgG and serum albumin are bound by FcRn at a slightly acidic pH (<6.5), and recycled to the cell surface where they are released at a neutral pH (>7.0) of blood. In this way IgG and serum albumin avoid lysosomal degradation. This mechanism provides an explanation for the greater serum circulation half-life of IgG and serum albumin. Thus, those antibodies that had increased binding of FcRn under simulated in vivo conditions would be expected to have a longer half-life and hence may represent superior therapeutic agents. A test system for determining the effects of HSA on antibody FcRn binding is shown in FIG. 13. FIG. 14 shows that HSA and mAb/HSA association steps produced a specific FcRn binding response at pH 6.0, which is fully reversible at pH 7.4. FIGS. 15A and 15B show that binding by mAb1 and mAb2 to FcRn is affected similarly by HSA. The effect is the same at low and physiological ionic strength. HSA diminishes mAb binding to FcRn at low and physiological HSA concentrations. The trials described below are generally carried out as described in Example 1.

Figure 16:
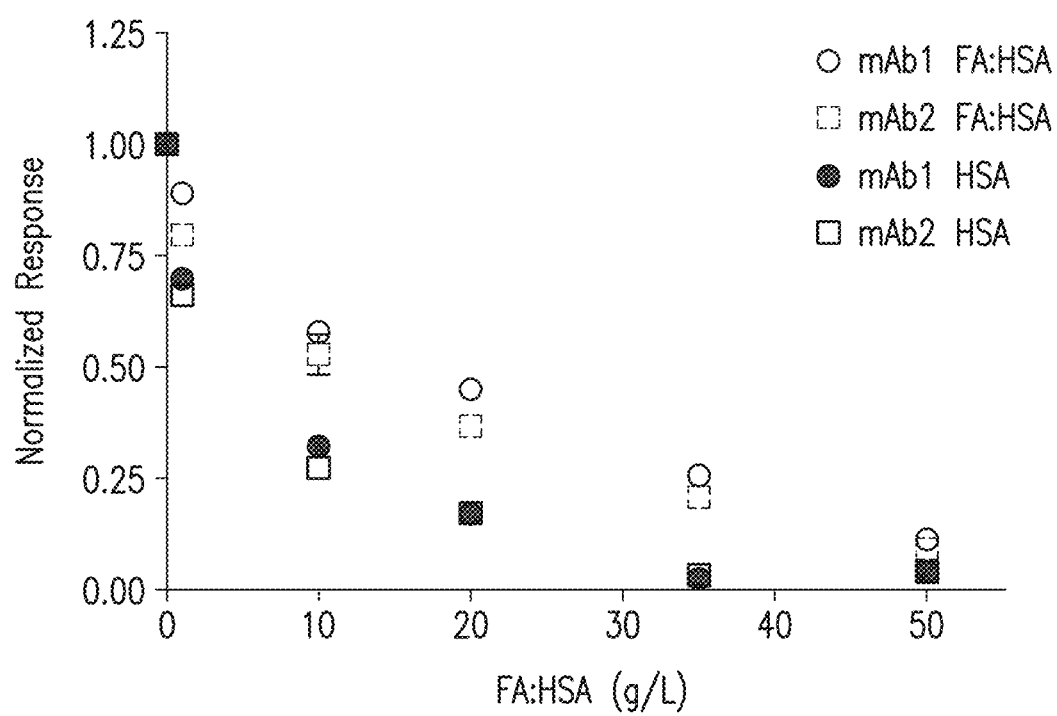
FIG. 16 is graph showing the dose-response curve effects of HSA for two different antibodies +/–FA.

Effect of FA loaded HSA on FcRn antibody binding: It has previously been reported that C18:1 abolished and C16:0 strongly reduced hFcRn binding, whereas C12:0 had a lesser effect, revealing that the recycling efficiency of FA-bound HSA is likely to be lower than that of ligand-free HSA. Here, experiments show (see FIG. 16) that the binding of two different mAbs (mAb1 and mAb2) to FcRn in presence of FA:HSA is higher compared to binding with pure HSA. This result suggests that pure HSA binds FcRn with higher affinity than 'dirty HSA', interfering with mAb interaction with FcRn. HSA loaded with FA may need to continue circulating, while ligand-free HSA requires recycling to the cytoplasm. The change in charge state of FA-bound HSA may result in decreased FcRn affinity.

Figure 18:
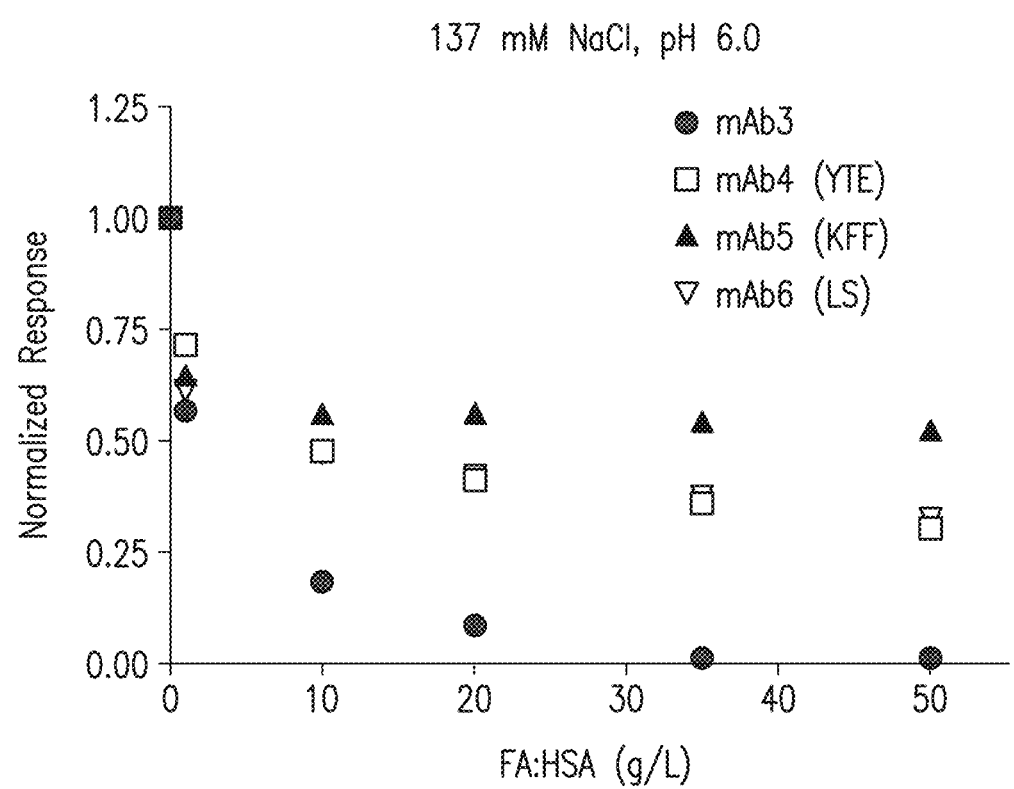
FIG. 18 is graph showing the dose-response curve effects of HSA on anti-O5 mAbs binding to FcRn.

Differential effect of HSA on anti-05 mAbs binding to FcRn: mAb3 is an anti-05 mAb. The half-life extended version of this mAb (mAb4) contains a YTE mutation (M252Y, S254T, T256E) (see FIG. 17). mAb5 and mAb6 contain HLE mutations KFF (H433K, N434F, Y436F) and LS (M428L, N434S), respectively. In contrast to the observations for mAb1 and mAb2, HSA affected various anti-05 molecules binding to FcRn differently (see FIG. 18). Although all molecules show diminished binding to FcRn in the presence of HSA, the HLE mutants (mAb4, mAb5, and mAb6) were affected to a lesser degree. mAb5 exhibited the least impact of HSA on FcRn binding, compared to the other HLE mutants.

Figure 19:
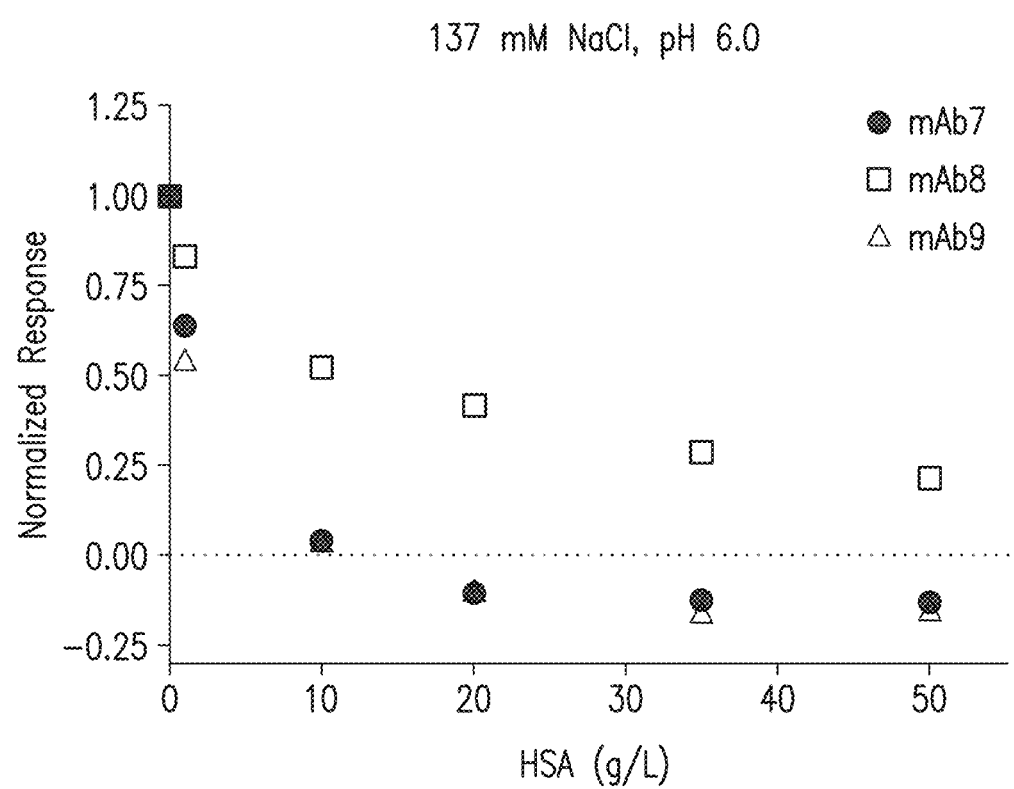
FIG. 19 is graph showing the dose-response curve effects of HSA on anti-Zika mAbs binding to FcRn.

Differential HSA effect on anti-Zika mAbs binding to FcRn: mAb7 is an anti-Zika mAb without Fcγ receptor binding activity. mAb8=mAb7+YTE mutation. mAb9 is an anti-Zika virus antibody with reduced Fcγ receptor binding activity. Only the YTE mutation affects interactions with FcRn. As shown in FIG. 19, mAb9 binding to FcRn is reduced at physiological levels of HSA; however, mAb9 maintained a higher degree of interaction with FcRn compared to mAb7 and mAb8 in the presence of HSA. At concentrations of 20 mg/mL HSA and above, mAb7 and mAb9 binding to FcRn was slightly obscured by the HSA signal (negative values).

Figure 20:
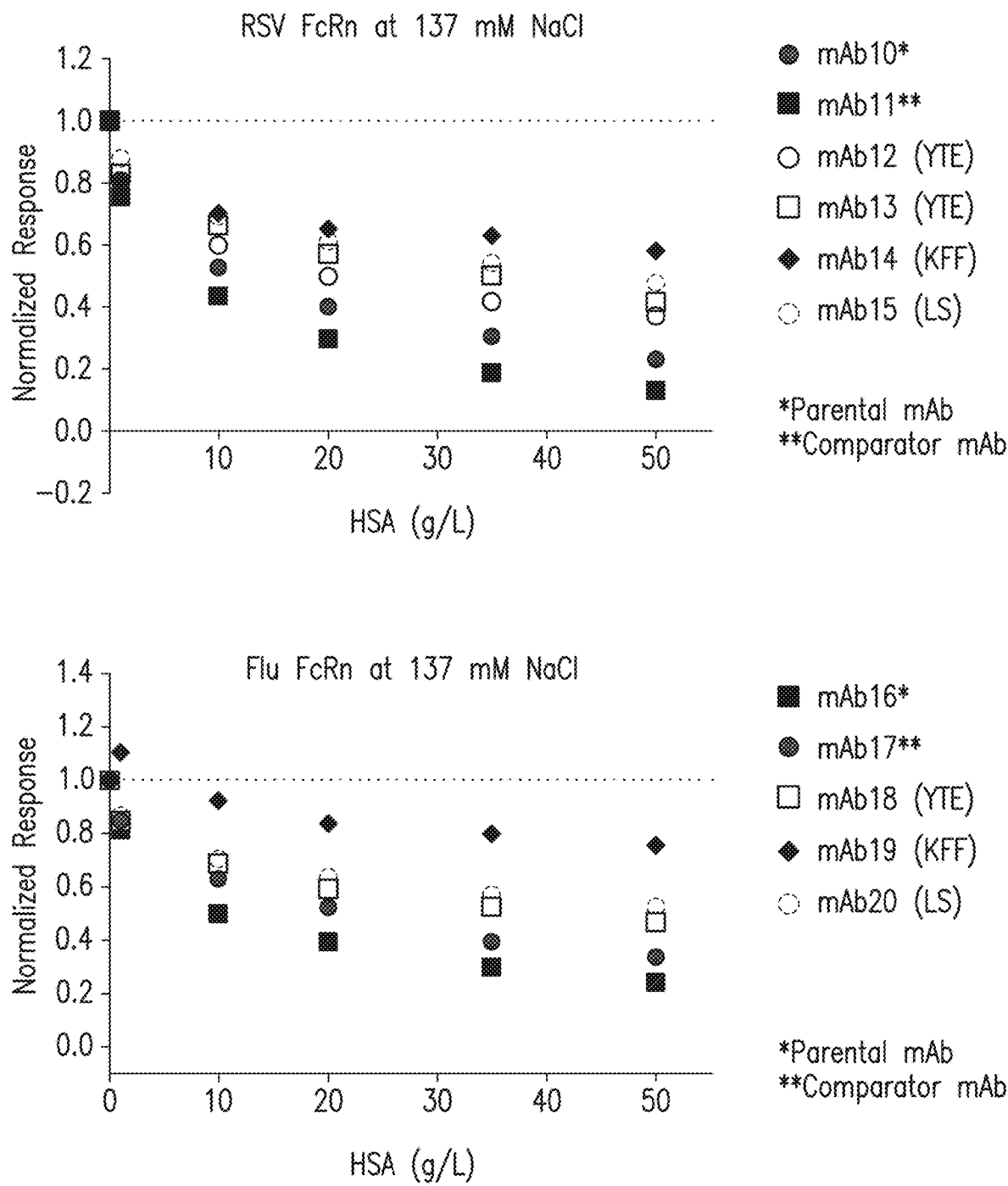
FIG. 20 is set of graphs showing the dose-response curve effects of HSA on half-life extension mutants.

Half-life extension mutants demonstrate a higher binding response to FcRn than parental mAbs in the presence of HSA: HLE mutants are designed to have a higher binding affinity to FcRn, and as demonstrated in FIG. 20 in the presence of HSA this rank ordering holds. KFF mutants show highest binding response under near physiological concentrations of HSA.

FcRn binding experiments demonstrate potential for using this platform as a tool to assess mAb function in physiological settings: Canonical BLI binding experiments showed that mAb1 and mAb2 have similar binding affinities for FcRn at both salt concentrations. HSA has a similar impact on FcRn binding by mAb1 and mAb2 at 10 and 137 mM NaCl. The presence of HSA diminished binding of mAb to FcRn. YTE mutants from anti-05 and anti-Zika antibodies demonstrated the increased binding affinity to FcRn as well as the reduced impact of HSA compared to 'wild-type'. This methodology can provide a platform to understand mAb function in a near-physiological setting, filling a space between Biophysical Developability Assessments and PK studies.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A method of determining an effect of non-specific interactions on monoclonal antibody-antigen interactions in simulated blood conditions, comprising:
   (a) contacting a solution comprising a blood protein and a monoclonal antibody with a biosensor, wherein a surface of the biosensor comprises an antigen that specifically binds to the monoclonal antibody, and wherein said blood protein does not specifically bind to said monoclonal antibody, wherein the blood protein is present at a concentration of between about 10 g/L and about 100 g/L;
   (b) allowing the monoclonal antibody to bind to the antigen;
   (c) determining an amount of the monoclonal antibody bound to the antigen using biolayer interferometry; and (d) comparing the amount of the monoclonal antibody bound to the antigen to a control threshold to determine an effect of non-specific interactions, wherein the control threshold is a normalized response to an ideal, dilute, or semi-dilute solution of the blood protein.

2. The method of claim 1, wherein the blood protein is selected from the group consisting of human serum albumin (HSA), IgG, transferrin, fibrinogen, IgA, α2-macroglobulin, IgM, α1-antitrypsin, haptoglobin, α1-acid glycoprotein, apolipoprotein A-1, and apolipoprotein A-11.

3. The method of claim 2, wherein the blood protein is present at a physiologically relevant concentration.

4. The method of claim 2, wherein the blood protein is present at a concentration of between about 10 g/L and about 80 g/L.

5. The method of claim 1, wherein the blood protein is human serum albumin.

6. The method of claim 1, further comprising determining an amount of binding at two or more concentrations of the blood protein.

7. The method of claim 1, further comprising determining an amount of binding at two or more pHs to determine a pH dependence of binding.

8. The method of claim 1, further comprising determining an amount of binding at two or more salt concentrations to determine a salt dependence of binding.

9. The method of claim 1, wherein the antigen is coupled to the surface of the sensor with a linker.

10. The method of claim 9, wherein the linker comprises biotin and streptavidin or avidin.

* * * * *